United States Patent
Cheng et al.

(10) Patent No.: US 12,102,721 B2
(45) Date of Patent: Oct. 1, 2024

(54) DOSAGE FORMS OF CONTROLLED RELEASE AT SPECIFIC GASTROINTESTINAL SITES

(71) Applicant: Triastek, Inc., Nanjing (CN)

(72) Inventors: Senping Cheng, Nanjing (CN); Xiaoling Li, Dublin, CA (US); Feihuang Deng, Nanjing (CN); Juan Yao, Nanjing (CN)

(73) Assignee: Triastek, Inc., Nanjing (CN)

( * ) Notice: Subject to any disclaimer, the term of this patent is extended or adjusted under 35 U.S.C. 154(b) by 0 days.

(21) Appl. No.: 16/481,036

(22) PCT Filed: Jan. 25, 2018

(86) PCT No.: PCT/CN2018/074146
§ 371 (c)(1),
(2) Date: Jul. 25, 2019

(87) PCT Pub. No.: WO2018/137686
PCT Pub. Date: Aug. 2, 2018

(65) Prior Publication Data
US 2021/0128479 A1    May 6, 2021

(30) Foreign Application Priority Data

Jan. 26, 2017 (CN) .......................... 201710057401.4

(51) Int. Cl.
*A61K 9/20* (2006.01)
*A61K 9/28* (2006.01)
*A61K 9/48* (2006.01)
*A61K 45/06* (2006.01)

(52) U.S. Cl.
CPC .......... *A61K 9/2086* (2013.01); *A61K 9/2806* (2013.01); *A61K 9/4808* (2013.01); *A61K 9/4816* (2013.01); *A61K 9/4833* (2013.01); *A61K 9/4891* (2013.01); *A61K 45/06* (2013.01)

(58) Field of Classification Search
CPC ................ A61K 9/2086; A61K 9/2806; A61K 9/4808; A61K 9/4816; A61K 9/4833; A61K 9/4891; A61K 45/06
See application file for complete search history.

(56) References Cited

U.S. PATENT DOCUMENTS

| | | |
|---|---|---|
| 3,823,816 A | 7/1974 | Controulis et al. |
| 4,735,804 A | 4/1988 | Caldwell et al. |
| 5,198,229 A | 3/1993 | Wong |
| 5,204,055 A | 4/1993 | Sachs |
| 5,260,009 A | 11/1993 | Penn |
| 5,340,656 A | 8/1994 | Sachs |
| 5,342,624 A | 8/1994 | Mcneill |
| 5,387,380 A | 2/1995 | Cima |
| 5,490,962 A | 2/1996 | Cima |
| 5,503,785 A | 4/1996 | Crump |
| 5,518,690 A | 5/1996 | Masahashi |
| 5,543,155 A | 8/1996 | Fekete |
| 5,633,021 A | 5/1997 | Brown |
| 5,869,170 A | 2/1999 | Cima |
| 6,264,985 B1 | 7/2001 | Cremer |
| 6,280,771 B1 | 8/2001 | Monkhouse |
| 6,294,200 B1 | 9/2001 | Conte et al. |
| 6,471,992 B1 | 10/2002 | Yoo |
| 6,514,518 B2 | 2/2003 | Monkhouse |
| 6,530,958 B1 | 3/2003 | Cima |
| 6,582,726 B1 | 6/2003 | Geysen |
| 6,685,962 B2 | 2/2004 | Friedman |
| 6,890,547 B1 | 5/2005 | Takada et al. |
| 7,163,693 B1 | 1/2007 | Clarke |
| 7,276,252 B2 | 10/2007 | Payumo |
| 7,300,668 B2 | 11/2007 | Pryce |
| 7,314,640 B2 | 1/2008 | Sriwongjanva et al. |
| 7,820,201 B2 | 10/2010 | Pryce |
| 7,875,290 B2 | 1/2011 | Payumo |
| 7,931,914 B2 | 4/2011 | Pryce |
| 8,088,415 B2 | 1/2012 | Wang |
| 8,465,777 B2 | 6/2013 | Wang |
| 8,673,352 B2 | 3/2014 | Sowden |
| 8,758,658 B2 | 6/2014 | Pryce Lewis |

(Continued)

FOREIGN PATENT DOCUMENTS

| | | |
|---|---|---|
| AU | 782141 B2 | 7/2005 |
| CN | 103948557 A | 7/2004 |
| CN | 1216597 C | 8/2005 |
| CN | 101370483 A | 2/2009 |
| CN | 1620284 B | 4/2010 |
| CN | 101990428 A | 3/2011 |
| CN | 105687153 A | 6/2016 |

(Continued)

OTHER PUBLICATIONS

Yoshida et al., pH- And Ion-Sensitive Polymers For Drug Delivery. Expert Opin Drug Deliv. 2013; 10(11): 1497-1513. (Year: 2013).*
Shende et al. Multi-layer Tablet: Current scenario and recent advances. International Journal of Drug Delivery 4 (2012) 418-426. (Year: 2012).*
Abdul et al. A flexible technology for modified release of drugs: multi layered tablets. Journal of Controlled Release 97 (2004):393-405. (Year: 2004).*
Brooke, D. et al. (Feb. 1977). "Zero-Order Drug Delivery System: Theory and Preliminary Testing," J. Pharm Sci. 66(2):159-162.
International Search Report, mailed Aug. 29, 2016 for PCT Application No. PCT/CN2016/084838, filed Jun. 3, 2016, 4 pages.

(Continued)

*Primary Examiner* — Robert A Wax
*Assistant Examiner* — Olga V. Tcherkasskaya
(74) *Attorney, Agent, or Firm* — MORRISON & FOERSTER LLP

(57) ABSTRACT

A dosage form of controlled release at specific gastrointestinal sites is provided. The dosage form includes a shell defining a first and a second compartment, a first active pharmaceutical ingredient (API) loaded in the first compartment, and a second API loaded in the second compartment, wherein the first API and the second API can be the same or different. The shell includes a first material soluble in a first gastrointestinal site and a second material soluble in a second gastrointestinal site.

11 Claims, 7 Drawing Sheets

(56) References Cited

U.S. PATENT DOCUMENTS

| | | |
|---|---|---|
| 8,828,411 B2 | 9/2014 | Yoo |
| 9,114,072 B2 | 8/2015 | Yoo |
| 9,314,429 B2 | 4/2016 | Jacob |
| 9,339,489 B2 | 5/2016 | Jacob |
| 10,143,626 B2 | 12/2018 | Li |
| 10,201,503 B1 | 2/2019 | Li |
| 10,258,575 B2 | 4/2019 | Li |
| 10,350,822 B1 | 7/2019 | Deng |
| 10,363,220 B2 | 7/2019 | Li |
| 10,624,857 B2 | 4/2020 | Li |
| 10,973,767 B2 | 4/2021 | Li |
| 11,278,499 B2 | 3/2022 | Li |
| 11,292,193 B2 | 4/2022 | Liu et al. |
| 11,364,674 B2 | 6/2022 | Cheng et al. |
| 11,383,439 B1 | 7/2022 | Liu |
| 11,458,684 B2 | 10/2022 | Liu et al. |
| 11,571,391 B2 | 2/2023 | Deng et al. |
| 11,612,569 B2 | 3/2023 | Li et al. |
| 2001/0051185 A1 | 12/2001 | Faour |
| 2002/0015728 A1 | 2/2002 | Payumo |
| 2002/0106412 A1 | 8/2002 | Rowe |
| 2003/0143268 A1 | 7/2003 | Pryce |
| 2003/0147952 A1 | 8/2003 | Lim |
| 2003/0198677 A1 | 10/2003 | Pryce |
| 2004/0005360 A1 | 1/2004 | Wang |
| 2005/0249798 A1 | 11/2005 | Mohammad |
| 2006/0099257 A1 | 5/2006 | Langridge et al. |
| 2006/0233881 A1 | 10/2006 | Sowden |
| 2008/0220061 A1 | 9/2008 | Pryce |
| 2008/0311191 A1* | 12/2008 | Nangia ............ A61K 31/522 424/463 |
| 2009/0148514 A1 | 6/2009 | Matthews et al. |
| 2009/0317465 A1 | 12/2009 | Peppas |
| 2010/0003332 A1 | 1/2010 | Bae et al. |
| 2010/0226855 A1* | 9/2010 | Nangia ............ A61K 9/0065 514/342 |
| 2010/0233253 A1 | 9/2010 | Kavimandan et al. |
| 2011/0111022 A1 | 5/2011 | Kim et al. |
| 2011/0187015 A1 | 8/2011 | Pryce |
| 2011/0262496 A1 | 10/2011 | Desai |
| 2012/0315333 A1 | 12/2012 | Zhou |
| 2013/0039960 A1 | 2/2013 | Desai |
| 2013/0193621 A1 | 8/2013 | Daya et al. |
| 2013/0337148 A1 | 12/2013 | Yang |
| 2013/0344149 A1 | 12/2013 | Stefan |
| 2014/0271842 A1 | 9/2014 | Herbig et al. |
| 2015/0366801 A1 | 12/2015 | Jacob |
| 2016/0354315 A1 | 12/2016 | Li |
| 2017/0027872 A1 | 2/2017 | Wen |
| 2018/0116911 A1 | 5/2018 | Li |
| 2018/0214383 A1 | 8/2018 | Sun et al. |
| 2018/0311167 A1 | 11/2018 | Li |
| 2019/0192440 A1 | 6/2019 | Li |
| 2019/0209468 A1 | 7/2019 | Deng |
| 2019/0209482 A1 | 7/2019 | Li |
| 2019/0321299 A1 | 10/2019 | Li et al. |
| 2020/0315971 A1 | 10/2020 | Li |
| 2020/0338009 A1 | 10/2020 | Li |
| 2021/0077410 A1 | 3/2021 | Deng et al. |
| 2021/0078244 A1 | 3/2021 | Deng et al. |
| 2021/0154910 A1 | 5/2021 | Cheng et al. |
| 2021/0178677 A1 | 6/2021 | Liu et al. |
| 2021/0196638 A1 | 7/2021 | Deng et al. |
| 2021/0205226 A1 | 7/2021 | Li |
| 2022/0118698 A1 | 4/2022 | Deng et al. |
| 2022/0212404 A1 | 7/2022 | Liu et al. |
| 2022/0212408 A1 | 7/2022 | Liu et al. |
| 2022/0339857 A1 | 10/2022 | Cheng et al. |
| 2023/0048362 A1 | 2/2023 | Liu et al. |
| 2023/0070928 A1 | 3/2023 | Wang et al. |
| 2023/0225978 A1 | 7/2023 | Li et al. |
| 2023/0398066 A1 | 12/2023 | Deng et al. |

FOREIGN PATENT DOCUMENTS

| | | |
|---|---|---|
| CN | 205343831 U | 6/2016 |
| CN | 106236715 A | 12/2016 |
| CN | 106491551 A | 3/2017 |
| CN | 107019676 A | 8/2017 |
| CN | 108215154 A | 6/2018 |
| CN | 207669820 U | 7/2018 |
| CN | 207901677 U | 9/2018 |
| CN | 105690762 A | 6/2019 |
| CN | 108215153 B | 8/2019 |
| CN | 110787145 A | 2/2020 |
| CN | 111249257 A | 6/2020 |
| EP | 0631775 A1 | 1/1995 |
| EP | 1112739 A1 | 7/2001 |
| EP | 3626439 A1 | 3/2020 |
| GB | 436236 A | 10/1935 |
| JP | H09221416 A | 8/1997 |
| JP | 2010523554 A | 7/2010 |
| JP | 2020506918 A | 3/2020 |
| JP | 2020507556 A | 3/2020 |
| WO | 199009168 A1 | 8/1990 |
| WO | 199213521 A1 | 8/1992 |
| WO | 199836738 A1 | 8/1998 |
| WO | 199836739 A1 | 8/1998 |
| WO | 2000015199 A1 | 3/2000 |
| WO | 200105406 A1 | 1/2001 |
| WO | 200137812 A2 | 5/2001 |
| WO | 200137813 A2 | 5/2001 |
| WO | 200187272 A2 | 11/2001 |
| WO | 2003037244 A2 | 5/2003 |
| WO | 2003037607 A1 | 5/2003 |
| WO | 2003041690 A2 | 5/2003 |
| WO | 2003092633 A2 | 11/2003 |
| WO | WO2004112755 A1 | 12/2004 |
| WO | 2005027878 A1 | 3/2005 |
| WO | 2006058247 A2 | 6/2006 |
| WO | 2007078290 A1 | 7/2007 |
| WO | 2008122966 A2 | 10/2008 |
| WO | 2009050189 A2 | 4/2009 |
| WO | 2009084040 A1 | 7/2009 |
| WO | 2009101658 A1 | 8/2009 |
| WO | 2009144558 A1 | 12/2009 |
| WO | 2014143935 A1 | 9/2014 |
| WO | 2014144512 A1 | 9/2014 |
| WO | 2014144661 A1 | 9/2014 |
| WO | 2015077262 A1 | 5/2015 |
| WO | 2015095230 A1 | 6/2015 |
| WO | 2015136377 A2 | 9/2015 |
| WO | 2015187746 A1 | 12/2015 |
| WO | 2016025762 A1 | 2/2016 |
| WO | 2016075497 A1 | 5/2016 |
| WO | WO2016192680 A1 | 12/2016 |
| WO | 2017152974 A1 | 9/2017 |
| WO | 2017153846 A2 | 9/2017 |
| WO | WO2017193099 A1 | 11/2017 |
| WO | 2018137686 A1 | 8/2018 |
| WO | WO2018137686 A9 | 8/2018 |
| WO | 2018210183 A1 | 11/2018 |
| WO | 2019025869 A1 | 2/2019 |
| WO | WO2019137199 A1 | 7/2019 |
| WO | WO2019137200 A1 | 7/2019 |
| WO | WO2019137333 A1 | 7/2019 |
| WO | 2019224058 A1 | 11/2019 |
| WO | 2021031824 A1 | 2/2021 |
| WO | 2021042865 A1 | 3/2021 |
| WO | 2021164660 A1 | 8/2021 |
| WO | 2022007570 A1 | 1/2022 |
| WO | 2022089631 A1 | 5/2022 |
| WO | 2022121927 A1 | 6/2022 |
| WO | 2022193922 A2 | 9/2022 |

OTHER PUBLICATIONS

Goyanes, A. et al. (2015), "3D Printing: Engineering Novel Oral Devices With Unique Design and Drug Release Characteristics," Molecular Pharmaceutics 12(11):3783-4174, 24 pages.

(56) References Cited

OTHER PUBLICATIONS

International Preliminary Report On Patentability, issued Dec. 5, 2017 for PCT Application No. PCT/CN2016/084838, filed Jun. 3, 2016, 5 pages.
Khaled, S.A. et al. (2015). "3D Printing of Five-In-One Dose Combination Polypill With Defined Immediate and Sustained Release Profiles," School of Pharmacy, The University of Nottingham 217:308-314, 21 pages.
Khaled, S.A. et al. (Oct. 30, 2015, e-pub. Jul. 30, 2015). "3D Printing of Tablets Containing Multiple Drugs With Defined Release Profiles," Int. J. Pharm 494(2):643-650.
Lipper, R.A. et al. (Feb. 1977). "Analysis Of Theoretical Behavior Of A Proposed Zero-Order Drug Delivery System," J. Pharm Sci. 66(2):163-164.
Srikonda, S. et al. (2006). "Osmotic Controlled Drug Delivery Systems," Chapter 7 in Design Of Controlled Release Drug Delivery Systems, pp. 203-230.
U.S. Appl. No. 16/614,301, filed Nov. 15, 2019, for Cheng et al. (Copy not submitted herewith pursuant to the waiver of 37 C.F.R. § 1.98(a)(2)(iii) issued by the Office on Sep. 21, 2004).
U.S. Appl. No. 16/904,893, Xiaoling Li, filed Jun. 18, 2020. (Copy not submitted herewith pursuant to the waiver of 37 C.F.R. § 1.98(a)(2)(iii) issued by the Office on Sep. 21, 2004).
U.S. Appl. No. 16/923,933, filed Jul. 8, 2020, for Li et al. (Copy not submitted herewith pursuant to the waiver of 37 C.F.R. § 1.98(a)(2)(iii) issued by the Office on Sep. 21, 2004).
U.S. Appl. No. 16/960,866, filed Jul. 8, 2020, for Deng et al. (Copy not submitted herewith pursuant to the waiver of 37 C.F.R. § 1.98(a)(2)(iii) issued by the Office on Sep. 21, 2004).
U.S. Appl. No. 16/960,867, filed Jul. 8, 2020, for Deng et al. (Copy not submitted herewith pursuant to the waiver of 37 C.F.R. § 1.98(a)(2)(iii) issued by the Office on Sep. 21, 2004).
Written Opinion Of The International Searching Authority, mailed Aug. 29, 2016 for PCT Application No. PCT/CN2016/084838, filed Jun. 3, 2016, 4 pages.
"Guidance For Industry: Dissolution Testing of Immediate Release Solid Oral Dosage Forms," Center for Drug Evaluation and Research, U.S. Food & Drug Administration. FDA-1997-D-0187, 17 pages. (Aug. 1997).
Gibson, L. et al. (2015) Additive Manufacturing Technologies: 3D Printing, Rapid Prototyping, and Direct Digital Manufacturing. 2 ed. Springer, New York, 6 pages.
Goole, J. et al. (Feb. 2016, e-pub. Jan. 3, 2016). "3D printing In Pharmaceutics: A New Tool For Designing Customized Drug Delivery Systems," Int. J. Pharm. 499(1-2):376-394.
International Preliminary Report on Patentability issued Jul. 30, 2019, for PCT Application No. PCT/CN2018/074146, filed Jan. 25, 2018, 5 pages.
International Search Report and Written Opinion, mailed Apr. 26, 2018, for PCT Application No. PCT/CN2018/074146, filed Jan. 25, 2018, 9 pages.
Katstra, W.E. et al. (Jun. 2001). "Fabrication of Complex Oral Delivery Forms By Three Dimensional Printing™," Dissertation in Materials Science and Engineering, Massachusetts Institute of Technology, 243 pages.
Katstra, W.E. et al. (May 3, 2000), "Oral Dosage Forms Fabricated By Three Dimensional Printing," J. Control Release 66:1-9.
Melchels, F.P.W. et al. (2010). "A Review On Stereolithography And Its Application In Biomedical Engineering," Biomaterials 31:6121-6130, 22 pages.
Rowe C.W. et al. (May 3, 2000). "Multimechanism oral Dosage Forms Fabricated By Three Dimensional Printing™" Journal Of Controlled Release 66(1):11-17.
U.S. Appl. No. 17/180,565, Liu et al., filed Feb. 19, 2021.(Copy not submitted herewith pursuant to the waiver of 37 C.F.R. § 1.98(a)(2)(iii) issued by the Office on Sep. 21, 2004).
U.S. Appl. No. 17/194,120, Feihuang et al., filed Mar. 5, 2021. (Copy not submitted herewith pursuant to the waiver of 37 C.F.R. § 1.98(a)(2)(iii) issued by the Office on Sep. 21, 2004).
U.S. Appl. No. 17/197,204, Li, X., filed Mar. 10, 2021.(Copy not submitted herewith pursuant to the waiver of 37 C.F.R. § 1.98(a)(2)(iii) issued by the Office on Sep. 21, 2004).
Meyer, D.M. et al. (2010). "Anti-Inflammatory Activity and Neutrophil Reductions Mediated by the JAK1/JAK3 Inhibitor, CP-690,550, in Rat Adjuvant-Induced Arthritis," J. Inflammation 7:41, 12 pages.
Rawlings, J.S. et al. (2004). "The JAK/STAT Signaling Pathway," J. Cell Sci. 117(8):1281-1823.
Schwartz, L. et al. (Jan. 1, 2017). "The Warburg Effect and the Hallmarks of Cancer," Nat Rev Drug Discov. 17(2):164-170, 26 pages.
Hatton, G. et al. (2015) "Animal Farm: Considerations in Animal Gastrointestinal Physiology and Relevance to Drug Delivery in Humans," J Pharm Sci. 104(9):2747-2776.
International Search Report and Written Opinion, mailed Jan. 30, 2022, for PCT Application No. PCT/CN2020/127852, filed Nov. 1, 2021, 15 pages.
International Search Report and Written Opinion, mailed Mar. 9, 2022, for PCT Application No. PCT/CN2020/136353, filed Dec. 8, 2021, 14 pages.
Thakral, S. et al. (2013). "Eudragit®: A Technology Evaluation," Expert Opin. Drug Deliv. 10(1):131-149.
Alhnan, M.A. et al. (Aug. 2016, e-published on May 18, 2016). "Emergence of 3D Printed Dosage Forms: Opportunities and Challenges," Pharm. Res. 33(8):1817-1832, 38 pages.
Ross, A.C. et al. (Feb. 18, 2000). "Chronopharmaceutical Drug Delivery from a Pulsatile Capsule Device Base on Programmable Erosion," Journal of Pharmacy and Pharmacology 52(8):903-909.
U.S. Appl. No. 18/034,004, filed Apr. 26, 2023, for Deng et al. (Copy not submitted herewith pursuant to the waiver of 37 C.F.R. § 1.98(a)(2)(iii) issued by the Office on Sep. 21, 2004).
U.S. Appl. No. 18/114,909, filed Feb. 27, 2023, for Li et al. (Copy not submitted herewith pursuant to the waiver of 37 C.F.R. § 1.98(a)(2)(iii) issued by the Office on Sep. 21, 2004).
U.S. Appl. No. 18/256,035, filed Jun. 5, 2023, for Deng et al. (Copy not submitted herewith pursuant to the waiver of 37 C.F.R. § 1.98(a)(2)(iii) issued by the Office on Sep. 21, 2004).
Cole, G. (1995). Pharmaceutical Coating Technology, Taylor & Francis Publishers, 553 pages.
Kempin, W. et al. (2018, e-pub. Apr. 20, 2018). "Immediate Release 3D-Printed Tablets Produced Via Fused Deposition Modeling of a Thermo-Sensitive Drug," Pharm. Res. 35:124, 12 pages.
U.S. Appl. No. 18/550,432, filed Sep. 13, 2023, for Cao et al. (Copy not submitted herewith pursuant to the waiver of 37 C.F.R. § 1.98(a)(2)(iii) issued by the Office on Sep. 21, 2004).

\* cited by examiner

DOSAGE FORMS OF CONTROLLED RELEASE AT SPECIFIC GASTROINTESTINAL SITES

CROSS-REFERENCE TO RELATED APPLICATION

This application is a national stage application under 35 U.S.C. § 371 of International Application No. PCT/CN2018/074146, filed internationally on Jan. 25, 2018, which claims priority to Chinese Patent Application No. 201710057401.4, filed Jan. 26, 2017, the entire disclosure of each of which is incorporated herein by reference in its entirety.

FIELD OF THE INVENTION

The present invention generally relates to drug dosage forms that can release drugs at certain gastrointestine sites.

BACKGROUND

Pharmaceutical drug products must be manufactured into dosage forms in order to be marketed for use. Drug dosage forms are specific configurations of drugs, such as tablets, capsules, injections, etc, that are used for the purposes of administration with specific routes or specific release sites. Depending on the routes and release sites of the dosage form, the drug may exhibit different effects. Categories of dosage forms, according to the states of the forms, include liquid dosage forms (e.g., solutions, syrups, elixirs, suspensions and emulsions), solid dosage forms (e.g., tablets, capsules, caplets and gel-caps), and semi-solid dosage form (e.g., ointments and suppositories). Among all the dosage forms, over 70% are solid dosage forms because they are advantageous in higher stability and easy to take and carry, which makes them the first choice in use and new drug development.

Oral routes are the most common routes for solid dosage forms, in which the dosage forms are administered orally, absorbed in the gastrointestinal tract to enter the circulation and distribute in the tissues to take effect. The gastrointestinal tract, which an orally administered drug must pass through, consists of three parts: stomach, small intestine and large intestine. Stomach is the most enlarged part of the digestive tract, which includes cardia that connects to esophageal, pylorus that connects to duodenum, and the body of the stomach between the cardia and the pylorus. Stomach controls the transportation of the contents in the stomach to intestine. Due to the lack of villus on the surface of stomach, stomach has limited absorption area and poor absorption for most drugs except some acidic drugs. Small intestine consists of duodenum, jejunum and ileum. Small intestine is the main absorption site of drugs, and also the specific site of active drug transportation. The pH of small intestine fluid is about 5-7.5, which is the best environment for absorption of weak alkaline drugs. Large intestine consists of cecum, colon and rectum. Large intestine is not only short and thick compared to small intestine, but also has only wrinkles and no villus on the surface mucosa. The effective absorption area of large intestine is much smaller than that of the small intestine. Drug absorption of large intestine is also worse than that of small intestine. Only some orally administered drugs that have slow absorption rate in stomach and small intestine are absorbed in large intestine.

After being absorbed in the gastrointestinal tract, drugs are partly metabolized in liver. Afterwards, the drug and its metabolites are excreted through the bile, kidney and other routes. Before reaching the systemic circulation from the administration site, drugs metabolize and decompose in gastrointestine tract, gastrointestinal wall and liver, thus decreasing the relative amount of drugs that enter the body. Therefore, many oral drugs have the problem of low bioavailability. If administered to patients with conventional dose, the drug into the systemic circulation after absorption may not achieve effective treatment or play a pharmacodynamic effect. One solution is to increase the dose of the drug to ensure that the effective amount of the drug is absorbed. However, this approach not only poses challenges to the pharmaceutical preparation process, but also increases the risk of drug side effects and poor patient compliance. On the other hand, if the drug's site of action is in the gastrointestinal tract, oral administration can theoretically increase the bioavailability of the drug. However, due to different retention and absorption efficiencies of drugs in various parts of the gastrointestinal tract, residence time is greatly influenced by the environment in the body. Therefore, oral drugs still have the problem of low local drug concentration on specific parts of the gastrointestinal tract (e.g., colon) and low bioavailability. Therefore, there is a need to design a new drug dosage form to improve the bioavailability.

BRIEF SUMMARY OF THE INVENTION

The present invention relates to design of dosage forms that is capable of controlling the release rates and release time under different gastrointestinal tract environment, thus allowing the drugs to be released and absorbed at specific gastrointestinal sites and increase the bioavailability of the drugs.

In one aspect, the present disclosure provides drug dosage form, which comprises a shell defining a first compartment and a second compartment, wherein said shell comprises a first material soluble at a first gastrointestinal site, and a second material soluble at a second gastrointestinal site; a first active pharmaceutical ingredient (API) loaded in the first compartment; and a second active pharmaloaded ingredient loaded in the second compartment.

In some embodiments, the first gastrointestinal site is the same as the second gastrointestinal site. In some embodiments, the first gastrointestinal site is different from the the second gastrointestinal site.

In some embodiments, the first API is the same as the second API. In some embodiments, the first API is different from the second API.

In some embodiments, the first or the second gastrointestinal site is stomach, small intestine or large intestine. In some embodiments, the first or the second gastrointestinal site is duodenum, jejunum or ileum. In some embodiments, the first or the second gastrointestinal site is cecum, colon or rectum.

In some embodiments, the first compartment is formed by the first material. In some embodiments, the second compartment is formed by the second material.

In some embodiments, the material described herein is a thermoplastic material. In some embodiments, the first or the second material is selected from the group consisting of EUDRAGIT® E (poly(butyl methacrylate, (2-dimethylaminoethyl) methacrylate, methyl methacrylate) 1:2:1), EUDRAGIT® L (poly(methacrylic acid, methyl methacrylate) 1:1), EUDRAGIT® S (poly(methacrylic acid, methyl methacrylate) 1:2), EUDRAGIT® FS (poly(methyl acrylate, methyl methacrylate, methacrylic acid) 7:3:1), polyvinylpyrrolidone (povidone), a copolymer of polyvinylpyrrolidone and polyvinyl acetate (copovidone), crospovidone, polyvinyl acetate Ester and povidone mixtures, methacrylic acid copolymers, aminomethacrylic acid copolymers, methacrylic acid ester copolymers, ethyl acrylate, a copolymer of anionic polymer and methacrylic acid, a copolymer of cationic polymer and di-methylaminoethyl methacrylate, butyl acrylate, a copolymer of methyl methacrylate and methyl acrylate, a copolymer of ethyl acrylate and methacrylate, a copolymer of butyl acrylate and methacrylate, a copolymer of ethyl acrylate and monomethacrylate ester, a copolymer of ethyl acrylate and methyl methacrylate, a copolymer of methyl methacrylate and trimethylaminoethyl methacrylate, ethyl acrylate/methyl methacrylate/chloride of methacrylic acid trimethylaminoethyl methacrylate polymer, methyl cellulose, ethyl cellulose, polyvinyl acetate phthalate, hypromellose succinate, polyethylene glycol-polyvinyl alcohol copolymer, hydroxypropyl methylcellulose phthalate formate or hypromellose phthalate, polyethylene glycol 15-hydroxystearate, a copolymer of methyl methacrylate and diethylaminoethyl methacrylate, a copolymer of polyacrylic acid methyl ester polymethylmethacrylate and polymethacrylic acid, N, N-dimethylaminoethylmethacrylate, a copolymer of polyvinylcaprolactam and polyvinyl acetate and polyethylene glycol graft, a copolymer of poly butyl methacrylate and poly-N,N-dimethylaminoethylmethacrylate and polymethylmethacrylate, polyvinyl alcohol, hydroxypropylcellulose, polyethylene oxide, polyoxyethylene hydrogenated castor oil, a copolymer of propylene oxide and ethylene oxide (poloxamer), polyethylene glycol, polyethylene glycol cetostearyl ether, hyperbranched polyesteramide, hydroxypropylmethylcellulose or hypromellose, hydroxyethylcellulose, cellulose acetate, polysorbate (Tween), carbomer, lactose, microcrystalline cellulose, pregelatinized starch, vitamins E polyethylene glycol succinate, polydimethylsiloxane, xanthan gum, polylactic acid, polylactide-polylactic acid copolymer, polycaprolactone, carnauba wax, glyceryl palmitostearate, hydrogenated castor oil, cellulose acetate butyrate, polyvinyl acetate, a copolymer of polyethyl acrylate and polymethylmethacrylate and polytrimethylammonium chloride ethyl methacrylate, a copolymer of polyethylene and polyvinyl acetate, chitosan, beeswax, polyethylene glycol methacrylate, and a combination thereof.

In some embodiments, the material described herein is a stomach soluble material. In some embodiments, the stomach soluble material is selected from the group consisting of EUDRAGIT® E (poly(butyl methacrylate, (2-dimethylaminoethyl) methacrylate, methyl methacrylate) 1:2:1), polyvinylpyrrolidone (povidone), a copolymer of polyvinylpyrrolidone and polyvinyl acetate (copovidone), crospovidone, mixtures of polyvinyl acetate and povidone, copolymers of methacrylic acid, a copolymer of aminomethacrylic acid, a copolymer of methacrylic acid ester, butyl acrylate, methacrylic acid methyl acrylate copolymer, a copolymer of methacrylic acid and ethyl acrylate, a copolymer of methacrylic acid and monobutyl acrylate, a copolymer of acrylic acid and ethyl methacrylate monomethacrylate, a copolymer of ethyl acrylate and monomethacrylate, ethyl acrylate/methyl methacrylate/trimethylaminoethyl methacrylate polymer, methyl cellulose, ethyl cellulose, polyvinyl acetate phthalate, hypromellose succinate, a copolymer of polyethylene glycol and polyvinyl alcohol, hydroxypropyl methylcellulose phthalate or hypromellose phthalate, polyethylene glycol 15-hydroxystearate, methyl methacrylate and diethylaminoethyl methacrylate copolymer, polymethyl acrylate-polymethylmethacrylate-polymethacrylate copolymer, polymethyl methacrylate, N-dimethylaminoethyl methacrylate, polyvinylcaprolactam-polyvinyl acetate-polyethylene glycol graft copolymer, polybutylmethacrylate-poly N,N-dimethylaminoethylmethacrylate-polymethylmethacrylate copolymer, polyvinyl alcohol, hydroxypropylcellulose, polyethylene oxide, polyoxyethylene, polyoxyethylene hydrogenated castor oil, a copolymer of propylene oxide and ethylene oxide (poloxamer), polyethylene glycol, polyethylene glycol cetostearyl ether, hyperbranched polyesteramides, hydroxypropylmethylcellulose or hypromellose, hydroxyethylcellulose, cellulose acetate, polysorbate (Tween), carbomer, lactose, microcrystalline cellulose, pregelatinized starch, vitamin E polyethylene glycol succinate, polydimethylsiloxane, xanthan gum, polylactic acid, polylactide-poly Lactic acid copolymer, polycaprolactone, carnauba wax, glyceryl palmitostearate, hydrogenated castor oil, cellulose acetate butyrate, polyvinyl acetate, polyethyl acrylate-polymethylmethacrylate-poly methyl ammonium chloride ethylmethacrylate copolymer, polyethylene-polyvinyl acetate copolymer, chitosan, beeswax, polyethylene glycol methacrylate, and a combination thereof.

In some embodiments, the material described herein is a small intestine soluble material. In some embodiments, the small intestine soluble material is selected from the group consisting of EUDRAGIT® L (poly(methacrylic acid, methyl methacrylate) 1:1), methacrylic acid copolymer, methacrylic acid ester copolymer, methacrylic acid-ethyl acrylate copolymer, copolymer of anionic polymer and methacrylic acid, a copolymer of cationic polymer and dimethylaminoethylmethacrylate ester, a copolymer of ethyl acrylate, methylmethacrylate and trimethylaminoethylmethacrylate, a neutral copolymer of ethyl acrylate and methylmethacrylate, hypromellose amber acid ester, methyl acrylate copolymer, ethyl acrylate copolymer, butyl acrylate copolymer, acrylate copolymer, methacrylate copolymer, and a combination thereof.

In some embodiments, the material described herein is a large intestine soluble material. In some embodiments, the large intestine soluble material is selected from the group consisting of EUDRAGIT® S (poly(methacrylic acid, methyl methacrylate) 1:2) or EUDRAGIT® FS (poly(methyl acrylate, methyl methacrylate, methacrylic acid) 7:3:1), methacrylic acid copolymer, methacrylic acid ester copolymer, methacrylic acid-ethyl acrylate copolymer, a copolymer of anionic polymer and methacrylic acid, a copolymer of cationic polymer and di-methylaminoethyl acrylate, a copolymer of ethyl acrylate, methyl methacrylate and trimethylaminoethyl methacrylate, a neutral copolymer of ethyl acrylate and methyl methacrylate, hydroxypropyl methyl cellulose succinate, methyl acrylate copolymer, ethyl acrylate copolymer, butyl acrylate copolymer, acrylate copolymer, methacrylate copolymer, and a combination thereof.

In some embodiments, the shell further comprises an insoluble material. In some embodiments, the insoluble material is selected from the group consisting of EUDRAGIT® RL (poly(ethyl acrylate, methyl methacrylate, trimethylammonioethyl methacrylate chloride) 1:2:0.2), EUDRAGIT® RS (poly(ethyl acrylate, methyl methacrylate, trimethylammonioethyl methacrylate chloride) 1:2:0.1), polyvinyl acetate and povidone mixtures, methacrylic acid copolymer, aminomethacrylic acid copolymer, methacrylic acid ester copolymer, butyl acrylate, methacrylic acid methylmethacrylate copolymer, ethyl methacrylate-co-methacrylic acid copolymer, butyl acrylate-monobutyl acrylate copolymer, ethyl acrylate-monomethacrylate copolymer, ethyl acrylate-methyl methacrylate copolymer, ethyl acrylate/methyl methacrylate/trimethylaminoethyl methacrylate polymer, methyl cellulose, ethyl cellulose, polyvinyl acetate phthalate, hypromellose succinate, polyethylene glycol-polyvinyl alcohol copolymer, hydroxypropyl methylcellulose phthalate or hypromellose phthalate, polyethylene glycol 15-hydroxystearate, a copolymer of methyl methacrylate and diethylaminoethylmethyl methacrylic acid ester, polymethyl acrylate-polymethyl methacrylate-polymethacrylic acid copolymer, N,N-dimethylaminoethylmethacrylate, polyvinylcaprolactam-polyvinyl acetate-polyethylene glycol graft copolymer, polybutyl methacrylate-poly N,N-dimethylaminoethyl methacrylate-polymethylmethacrylate copolymer, polyvinyl alcohol, polyethylene oxide, polyoxyethylene, hyperbranched polyesteramides, hydroxypropylmethylcellulose or hypromellose, hydroxyethylcellulose, cellulose acetate, vitamin E polyethylene glycol succinate, polydimethylsiloxane alkane, xanthan gum, polylactic acid, polylactide-polylactic acid copolymer, polycaprolactone, carnauba wax, glyceryl palmitostearate, hydrogenated castor oil, cellulose acetate butyrate, polyvinyl acetate, polyethyl acrylate-polymethylmethacrylate-polytrimethylammonium chloride ethyl methacrylate copolymer, polyethylene-polyvinyl acetate copolymer, chitosan, and a combination thereof.

In some embodiments, the insoluble material forms the first or the second compartment together with the first or the second material. In some embodiments, the first or the second compartment has an opening covered by the first or the second material, and wherein the insoluble material forms rest part of the first or the second compartment except the opening.

In some embodiments, the first material forms the first compartment, wherein the second compartment forms the second compartment, wherein the first material further forms a third compartment, and wherein the second material is located in the third compartment. In certain embodiments, the first compartment is the same as the third compartment. In some embodiments, the first compartment and the third compartment are independent and separate compartments. In some embodiments, the first material forms the first compartment, the second material forms the second compartment, wherein the first API forms a third compartment, and wherein the second material is located in the third compartment.

In some embodiments, the compartment described herein is configured as a shape selected from the group consisting of a pie shape, a cone shape, a pyramid shape, a cylindrical shape, a cubic or cuboidal shape, a triangular or polygonal prism shape, a tetrahedron and a combination thereof. In some embodiments, the compartment has a pie shape and an opening, wherein the opening is covered by the stomach soluble, small intestine soluble or colon soluble material, and wherein the insoluble material forms rest part of the first compartment except the opening.

In some embodiments, the drug dosage form further comprises a third API and the shell further defines a third compartment, wherein the shell further comprises a third material soluble in a third gastrointestinal site, wherein the third API is loaded in the the third compartment. In some embodiments, the third gastrointestinal site is the same as the first or the second gastrointestinal site. In some embodiments, the third gastrointestinal site is different from the first and the second gastrointestinal site. In some embodiments, the first, the second and the third APIs are the same. In some embodiments, the first, the second and the third APIs are different from each other. In some embodiments, the first material is a stomach soluble material, the second material is a small intestine soluble material and the third material is a large intestine material. In some embodiments, the first material forms the first compartment, the second material forms the second compartment and the third material forms the third compartment. In some embodiments, the first material further forms a fourth compartment, and wherein the second material locates in the fourth compartment. In some embodiments, the first API forms a fourth compartment, and wherein the second material locates in the fourth compartment. In some embodiments, the first material further forms a fourth compartment and a fifth compartment, wherein the second material locates in the fourth compartment, and wherein the third material locates in the fifth compartment. In some embodiments, the first API forms a fourth compartment and a fifth compartment, wherein the second material locates in the fourth compartment, and wherein the third material locates in the fifth compartment. In some embodiments, the first API forms a fourth compartment, wherein the second API forms a fifth compartment, wherein the second material locates in the fourth compartment, and wherein the third material locates in the fifth compartment. In some embodiments, the first, the second and the third materials are juxtaposed. In some embodiments, the shell further comprises an insoluble material, and wherein the insoluble material is attached to the first, the second and the third material.

In some embodiments, the drug dosage form comprises a shell that defines a first compartment, a second compartment and a third compartment, wherein the first, the second and the third compartments have a pie shape, wherein the first compartment has a first opening covered by a first material soluble in a first gastrointestinal site, wherein the second compartment has a second opening covered by a second material soluble in a second gastrointestinal site, wherein the third compartment has a third opening covered by a third material soluble in a third gastrointestinal site, and wherein an insoluble material forms rest part of the first, the second and the third compartments except the first, the second and the third openings. In some embodiments, the first material is a stomach soluble material, the second material is a small intestine soluble material, and the third material is a large intestine soluble material.

In some embodiments, the drug dosage form comprises a cylindrical shell defining a cavity, the cylindrical shell having an upper end and a bottom end, wherein the cylindrical shell is formed by an insoluble material, and wherein the upper and the bottom ends are covered by a first material soluble in a first gastrointestinal site; and a first and a second APIs, both loaded in the cavity, wherein the first and the second APIs are separated by a second material soluble in a second gastrointestinal site, wherein the first material, the first API, the second material and the second material are configured as a multi-layered structure. In some embodiments, the first material is a stomach soluble material, and the second material is a large intestine soluble material. In some embodiments, the first material is a large intestine soluble material. In some embodiments, first material is a colon soluble material.

In some embodiments, the API described herein is selected from the group consisting of local anesthetics, antiepileptic drugs and anticonvulsants, pain management drugs, sleeping disorder drugs, anti-Alzheimer's disease drugs, analgesics, antipodagric, anti-hypertensive drugs, antiarrhythmic drugs, diuretic drugs, drugs for treating liver diseases, drugs for treating pancreatic diseases, drugs for treating gastrointestinal diseases, drugs for treating CNS diseases, antihistamine drugs, anti-allergic drugs, glucocorticoid drugs, hormone drugs and contraceptive drugs, hypoglycemic drugs, anti-osteoporosis drugs, antibiotics, sulfonamides, quinolones, and other synthetic antibacterial drugs, antituberculous drugs, antiviral drugs, anti-neoplasm drugs, immunomodulators, veterinary drugs, cosmetically active agents, nutritional agent, chemical reagents, traditional Chinese medicine and extract of traditional Chinese medicine.

In another aspect, the present disclosure provides a drug dosage form, which comprises a first particle, wherein the first particle comprises a first API wrapped by a first coat, wherein the first coat has a first thickness and dissolves at a first gastrointestinal site to release the first API; a second particle, wherein the second particle comprises a second API wrapped by a second coat, wherein the second coat has a second thickness and dissolves at a second gastrointestinal site to release the second API; a third particle, wherein the third particle comprises a third API wrapped by a third coat, wherein the third coat has a third thickness and dissolves at a third gastrointestinal site to release the third API; and a shell defining a compartment, wherein the first, the second and the third particles locate in the compartment.

In some embodiments, the first, the second or the third coats are formed by a material selected from the group consisting of polyvinylpyrrolidone (povidone), polyvinylpyrrolidone-polyvinyl acetate copolymer (copovidone), crospovidone, mixtures of polyvinyl acetate and povidone, methacrylic acid copolymers, aminomethyl Acrylic acid copolymer, methacrylic acid ester copolymer, ethyl acrylate, a copolymer of an anionic polymer and methacrylic acid, a copolymer of a cationic polymer and dimethylaminoethyl methacrylate, a butyl acrylate, a copolymer of methacrylic acid and methyl acrylate, ethyl methacrylate copolymer, butyl methacrylate copolymer, an ethyl acrylate monomethacrylate copolymer, an ethyl acrylate monomethacrylate copolymer, a copolymer of methyl methacrylate and trimethylaminoethyl methacrylate, ethyl acrylate/methyl methacrylate/trimethylaminoethyl methacrylate polymers, methyl cellulose, ethyl Cellulose, polyvinyl acetate phthalate, hypromellose succinate, polyethylene glycol-polyvinyl alcohol copolymer, hydroxypropyl methylcellulose phthalate or hypromellose phthalate, polyethylene glycol 15-hydroxystearate, methyl methacrylate and diethylaminoethyl methacrylate copolymer, polymethyl acrylate-polymethylmethacrylate-polymethacrylate copolymer, polymethyl methacrylate, N-dimethylaminoethyl methacrylate, polyvinylcaprolactam-polyvinyl acetate-polyethylene glycol graft copolymer, polybutylmethacrylate-poly N,N-dimethylaminoethylmethacrylate-polymethylmethacrylate copolymer, polyvinyl alcohol, hydroxypropylcellulose, polyethylene oxide, polyoxyethylene, polyoxyethylene hydrogenated castor oil, a copolymer of propylene oxide and ethylene oxide (poloxamer), polyethylene glycol, polyethylene glycol cetostearyl ether, hyperbranched polyesteramide, hydroxypropyl Methyl cellulose or hypromellose, hydroxyethyl cellulose, cellulose acetate, polysorbate (Tween), carbomer, lactose, microcrystalline cellulose, pregelatinized starch, vitamin E polyethylene glycol alcohol succinate, polydimethylsiloxane, xanthan gum, polylactic acid, polylactide-polylactic acid copolymer, polycaprolactone, carnauba wax, glyceryl palmitostearate, hydrogenated castor oil, Cellulose acetate butyrate, polyvinyl acetate, polyethylacrylate-polymethylmethacrylate-polytrimethylammonium chloride ethylmethacrylate copolymer, polyethylene-polyvinyl acetate copolymer and shell poly Sugar, beeswax, polyethylene glycol methacrylate, and combinations thereof.

In some embodiments, the thickness of the coat describe herein is 0.05 mm-10 mm.

In some embodiments, the first API, the second API and the third API are the same. In some embodiments, the first API, the second API and the third API are different from each other.

BRIEF DESCRIPTION OF THE DRAWINGS

FIG. 10A shows an exemplary dosage form having a substrate forming three column-shaped compartments. Each compartment is loaded with one drug content. Each drug content has a plug that blocks the aperture of each compartment.

DETAILED DESCRIPTION OF THE INVENTION

Figure 1:
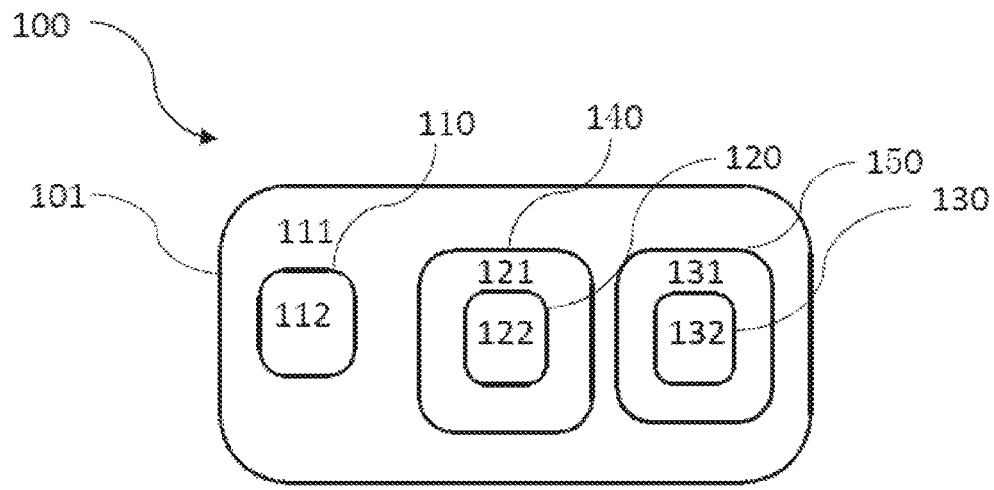
FIG. 1 shows an exemplary drug dosage form of controlled release at specific gastrointestinal site.

In the Summary of the Invention above and in the Detailed Description of the Invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or particular claim, that feature can also be used, to the extent possible, in combination with and/or in the context of other particular aspects and embodiments of the invention, and in the invention generally.

Definitions

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Where a range of value is provided, it is understood that each intervening value, to the tenth of the unit of the lower limit unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

The term "about" as used herein when referring to a measurable value such as an amount, a temporal duration, and the like, is meant to encompass variations of up to ±10% from the specified value. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the disclosed subject matter. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. In this disclosure, when a range is given as "(a first number) to (a second number)" or "(a first number)-(a second number)," this means a range whose lower limit is the first number and whose upper limit is the second number. For example, 2 to 10 millimeters means a range whose lower limit is 2 millimeters, and whose upper limit is 10 millimeters.

As used herein, "attach" or "attachment" refers to an object A links to another object B in any manner. The attachment can be direct or indirect. The direct attachment means the object A and the object B at least partly contact directly to form an integral structure. The indirect attachment means the object A does not contact to the object B directly, but link through an object C to form a whole.

As used herein, "configuration" refers to the design for the shape, structure, dimensions, thickness, composition, etc. of an object.

Drug Dosage Forms

In one aspect, the present disclosure provides drug dosage form that can control the release of the drugs contained within at specific gastrointestine sites.

The gastrointestine site refers to any site in the gastrointestinal tract, including stomach, small intestine (including duodenum, jejunum and ileum) and large intestine (including cecum, colon and rectum).

The drug dosage forms described herein may be, for example, any size, shape, or weight that is suitable for oral administration. In some embodiments, the drug dosage form is suitable for oral administration to an individual, wherein the size, shape, and/or weight of the drug dosage form is based on an attribute of the individual. In some embodiments, the attribute of an individual is one or more of height, weight, or age. In some embodiments, the individual is an infant. In some embodiments, the individual is a child. In some embodiments, the individual is an adolescent. In some embodiments, the individual is an adult.

In some embodiments, the largest dimension crossing a drug dosage form, e.g., largest diameter, is about 1 mm to about 25 mm, such as any of about 2 mm to about 10 mm, about 5 mm to about 12 mm, about 8 mm to about 15 mm, about 5 mm to about 10 mm, or about 7 mm to about 9 mm. In some embodiments, the largest dimension crossing a drug dosage form, e.g., largest diameter, is less than about 25 mm, such as less than about any of 24 mm, 23 mm, 22 mm, 21 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, 5 mm, 4 mm, 3 mm, 2 mm, or 1 mm. In some embodiments, the largest dimension crossing a drug dosage form, e.g., largest diameter, is greater than about 1 mm, such as greater than about any of 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm. In some embodiments, the largest dimension crossing a drug dosage form, e.g., largest diameter, is about any of 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm.

In some embodiments, the drug dosage form has a thickness of about 1 mm to about 25 mm, such as any of about 2 mm to about 10 mm, about 5 mm to about 12 mm, about 8 mm to about 15 mm, about 5 mm to about 10 mm, or about 7 mm to about 9 mm. In some embodiments, the drug dosage form has a thickness of less than about 25 mm, such as less than about any of 24 mm, 23 mm, 22 mm, 21 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, 5 mm, 4 mm, 3 mm, 2 mm, or 1 mm. In some embodiments, the drug dosage form has a thickness of greater than about 1 mm, such as greater than about any of 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm. In some embodiments, the drug dosage form has a thickness of about any of 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm.

In some embodiments, the shape of a drug dosage form comprises a cylinder, oval, bullet shape, arrow head shape, triangle, arced triangle, square, arced square, rectangle, arced rectangle, diamond, pentagon, hexagon, octagon, half moon, almond, or a combination thereof.

In some embodiments, the shape of a drug dosage form comprises a cylinder, oval, bullet shape, arrow head shape, triangle, arced triangle, square, arced square, rectangle, arced rectangle, diamond, pentagon, hexagon, octagon, half moon, almond, or a combination thereof, wherein the largest dimension crossing the drug dosage form, e.g., largest diameter, is about any of 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm.

In some embodiments, the total weight of a drug dosage form is about 20 mg to about 1500 mg, such as about any of about 50 mg to about 150 mg, about 150 mg to about 250 mg, about 160 mg to about 170 mg, about 250 mg to about 350 mg, about 350 mg to about 450 mg, about 450 mg to about 550 mg, about 550 mg to about 650 mg, about 650 mg to about 750 mg, about 750 mg to about 850 mg, about 850 mg to about 950 mg, about 950 mg to about 1050 mg, about 1050 mg to about 1150 mg, about 1150 mg to about 1250 mg, about 1250 mg to about 1350 mg, or about 1350 mg to about 1450 mg. In some embodiments, the total weight of a drug dosage form is less than about 1500 mg, such as less than about any of 1450 mg, 1400 mg, 1350 mg, 1300 mg, 1250 mg, 1200 mg, 1150 mg, 1100 mg, 1050 mg, 1000 mg, 950 mg, 900 mg, 850 mg, 800 mg, 750 mg, 700 mg, 650 mg, 600 mg, 550 mg, 500 mg, 475 mg, 450 mg, 425 mg, 400 mg, 375 mg, 350 mg, 325 mg, 300 mg, 275 mg, 250 mg, 225 mg, 200 mg, 175 mg, 150 mg, 125 mg, 100 mg, 95 mg, 90 mg, 85 mg, 80 mg, 75 mg, 70 mg, 65 mg, 60 mg, 55 mg, 50 mg, 45 mg, 40 mg, 35 mg, 30 mg, or 25 mg. In some embodiments, the total weight of a drug dosage form is greater than about 20 mg, such as greater than about any of 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, or 1450 mg. In some embodiments, the total weight of a drug dosage form is about any of 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 160 mg, 165 mg, 170 mg, 175 mg, 200 mg, 225 mg, 250 mg, 275 mg, 300 mg, 325 mg, 350 mg, 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, or 1450 mg.

The drug dosage forms of the present disclosure can further be coated, such as embedded, encased, or attached thereto, to, for example, (a) modify the taste, odor, and/or color of the drug dosage form; (b) protect the components of the drug dosage form from light, moisture, and/or air; (c) control the release of the components of the drug dosage form; (d) improve and/or alter the external appearance of the drug dosage form; (e) adjust position of drug release; (f) adjust texture of the drug dosage form; and (g) provide abuse deterrent features to the drug dosage form. In some embodiments, at least a portion of a drug dosage form is coated, such as embedded, encased, or attached thereto. In some embodiments, the drug dosage form is coated, such as embedded, encased, or attached thereto, with a sugar coating, e.g., an erodible material comprising sugar. In some embodiments, the drug dosage form is coated, such as embedded, encased, or attached thereto, with a film. In some embodiments, the drug dosage form is coated, such as embedded, encased, or attached thereto, with an enteric coating. In some embodiments, the drug dosage form is coated, such as embedded, encased, or attached thereto, with a gelatin layer.

In some embodiments, the drug dosage form has a surface area of about 20 mm$^2$ to about 700 mm$^2$. In some embodiments, the drug dosage form has a surface area of at least about 20 mm$^2$, such as at least about any of 30 mm$^2$, 40 mm$^2$, 50 mm$^2$, 60 mm$^2$, 70 mm$^2$, 80 mm$^2$, 90 mm$^2$, 100 mm$^2$, 125 mm$^2$, 150 mm$^2$, 175 mm$^2$, 200 mm$^2$, 225 mm$^2$, 250 mm$^2$, 275 mm$^2$, 300 mm$^2$, 325 mm$^2$, 350 mm$^2$, 375 mm$^2$, 400 mm$^2$, 425 mm$^2$, 450 mm$^2$, 475 mm$^2$, 500 mm$^2$, 525 mm$^2$, 550 mm$^2$, 575 mm$^2$, 600 mm$^2$, 625 mm$^2$, 650 mm$^2$, 675 mm$^2$, or 700 mm$^2$. In some embodiments, the drug dosage form has a surface area of less than about 700 mm$^2$, such as less than about any of 675 mm$^2$, 650 mm$^2$, 625 mm$^2$, 600 mm$^2$, 575 mm$^2$, 550 mm$^2$, 525 mm$^2$, 500 mm$^2$, 475 mm$^2$, 450 mm$^2$, 425 mm$^2$, 400 mm$^2$, 375 mm$^2$, 350 mm$^2$, 325 mm$^2$, 300 mm$^2$, 275 mm$^2$, 250 mm$^2$, 225 mm$^2$, 200 mm$^2$, 175 mm$^2$, 150 mm$^2$, 125 mm$^2$, 100 mm$^2$, 90 mm$^2$, 80 mm$^2$, 70 mm$^2$, 60 mm$^2$, 50 mm$^2$, 40 mm$^2$, or 30 mm$^2$. In some embodiments, the drug dosage form has a surface area of about any of 700 mm$^2$, 675 mm$^2$, 650 mm$^2$, 625 mm$^2$, 600 mm$^2$, 575 mm$^2$, 550 mm$^2$, 525 mm$^2$, 500 mm$^2$, 475 mm$^2$, 450 mm$^2$, 425 mm$^2$, 400 mm$^2$, 375 mm$^2$, 350 mm$^2$, 325 mm$^2$, 300 mm$^2$, 275 mm$^2$, 250 mm$^2$, 225 mm$^2$, 200 mm$^2$, 175 mm$^2$, 150 mm$^2$, 125 mm$^2$, 100 mm$^2$, 90 mm$^2$, 80 mm$^2$, 70 mm$^2$, 60 mm$^2$, 50 mm$^2$, 40 mm$^2$, 30 mm$^2$, or 20 mm$^2$.

Materials Dissolvable at Specific GI Sites.

In some embodiments, the drug dosage forms described herein comprises materials dissolvable at specific GI sites, including stomach soluble materials, small intestine (e.g., duodenum, jejunum and ileum) soluble materials, large intestine (e.g., cecum, colon and rectum) soluble materials and insoluble materials.

As used herein, "stomach soluble materials" refer to materials that can dissolve in gastric fluid when retained in stomach (usually less than 6 hours). Stomach soluble materials include without limitation: EUDRAGIT® E (poly (butyl methacrylate, (2-dimethylaminoethyl) methacrylate, methyl methacrylate) 1:2:1), polyvinylpyrrolidone (povidone), a copolymer of polyvinylpyrrolidone and polyvinyl acetate (copovidone), crospovidone, mixtures of polyvinyl acetate and povidone, copolymers of methacrylic acid, a copolymer of aminomethacrylic acid, a copolymer of methacrylic acid ester, butyl acrylate, methacrylic acid methyl acrylate copolymer, a copolymer of methacrylic acid and ethyl acrylate, a copolymer of methacrylic acid and monobutyl acrylate, a copolymer of acrylic acid and ethyl methacrylate monomethacrylate, a copolymer of ethyl acrylate and monomethacrylate, ethyl acrylate/methyl methacrylate/trimethylaminoethyl methacrylate polymer, methyl cellulose, ethyl cellulose, polyvinyl acetate phthalate, hypromellose succinate, a copolymer of polyethylene glycol and polyvinyl alcohol, hydroxypropyl methylcellulose phthalate or hypromellose phthalate, polyethylene glycol 15-hydroxystearate, methyl methacrylate and diethylaminoethyl methacrylate copolymer, polymethyl acrylate-polymethylmethacrylate-polymethacrylate copolymer, polymethyl methacrylate, N-dimethylaminoethyl methacrylate, polyvinylcaprolactam-polyvinyl acetate-polyethylene glycol graft copolymer, polybutylmethacrylate-poly N,N-dimethylaminoethylmethacrylate-polymethylmethacrylate copolymer, polyvinyl alcohol, hydroxypropylcellulose, polyethylene oxide, polyoxyethylene, polyoxyethylene hydrogenated castor oil, a copolymer of propylene oxide and ethylene oxide (poloxamer), polyethylene glycol, polyethylene glycol cetostearyl ether, hyperbranched polyesteramides, hydroxypropylmethylcellulose or hypromellose, hydroxyethylcellulose, cellulose acetate, polysorbate (Tween), carbomer, lactose, microcrystalline cellulose, pregelatinized starch, vitamin E polyethylene glycol succinate, polydimethylsiloxane, xanthan gum, polylactic acid, polylactide-poly Lactic acid copolymer, polycaprolactone, carnauba wax, glyceryl palmitostearate, hydrogenated castor oil, cellulose acetate butyrate, polyvinyl acetate, polyethyl acrylate-polymethylmethacrylate-poly methyl ammonium chloride ethylmethacrylate copolymer, polyethylene-polyvinyl acetate copolymer, chitosan, beeswax, polyethylene glycol methacrylate, and a combination thereof.

As used herein, "small intestine soluble materials" refer to materials that can dissolve in the small intestine environment when they are retained in the small intestine. In some embodiments, small intestine soluble materials refer to materials that cannot dissolve in gastric fluid when it is retained in the stomach but can dissolve in the small intestine environment. Small intestine soluble materials include without limitation: EUDRAGIT® L (poly(methacrylic acid, methyl methacrylate) 1:1), methacrylic acid copolymer, methacrylic acid ester copolymer, methacrylic acid-ethyl acrylate copolymer, copolymer of anionic polymer and methacrylic acid, a copolymer of cationic polymer and dimethylaminoethylmethacrylate ester, a copolymer of ethyl acrylate, methylmethacrylate and trimethylaminoethylmethacrylate, a neutral copolymer of ethyl acrylate and methylmethacrylate, hypromellose amber acid ester, methyl acrylate copolymer, ethyl acrylate copolymer, butyl acrylate copolymer, acrylate copolymer, methacrylate copolymer, and a combination thereof.

As used herein, "large intestine soluble materials" refer materials that can dissolve in the large intestine environment when it is retained in the large intestine environment. In some embodiments, large intestine soluble materials refer to materials that cannot dissolve in gastric fluid when they are retained in the stomach or dissolve in small intestine environment when they are retained in the small intestine but can dissolve in the large intestine environment. Large intestine soluble materials include without limitation: EUDRAGIT® S (poly(methacrylic acid, methyl methacrylate) 1:2) or EUDRAGIT® FS (poly(methyl acrylate, methyl methacrylate, methacrylic acid) 7:3:1), methacrylic acid copolymer, methacrylic acid ester copolymer, methacrylic acid-ethyl acrylate copolymer, a copolymer of anionic polymer and methacrylic acid, a copolymer of cationic polymer and di-methylaminoethyl acrylate, a copolymer of ethyl acrylate, methyl methacrylate and trimethylaminoethyl methacrylate, a neutral copolymer of ethyl acrylate and methyl methacrylate, hydroxypropyl methyl cellulose succinate, methyl acrylate copolymer, ethyl acrylate copolymer, butyl acrylate copolymer, acrylate copolymer, methacrylate copolymer, and a combination thereof.

As used herein, "insoluble materials" refer to materials that do not dissolve in the gastrointestinal tract environment when they are retained in gastrointestinal tract. Insoluble materials include without limitation: EUDRAGIT® RL (poly(ethyl acrylate, methyl methacrylate, trimethylammonioethyl methacrylate chloride) 1:2:0.2), EUDRAGIT® RS (poly(ethyl acrylate, methyl methacrylate, trimethylammonioethyl methacrylate chloride) 1:2:0.1), polyvinyl acetate and povidone mixtures, methacrylic acid copolymer, aminomethacrylic acid copolymer, methacrylic acid ester copolymer, butyl acrylate, methacrylic acid methylmethacrylate copolymer, ethyl methacrylate-co-methacrylic acid copolymer, butyl acrylate-monobutyl acrylate copolymer, ethyl acrylate-monomethacrylate copolymer, ethyl acrylate-methyl methacrylate copolymer, ethyl acrylate/methyl methacrylate/trimethylaminoethyl methacrylate polymer, methyl cellulose, ethyl cellulose, polyvinyl acetate phthalate, hypromellose succinate, polyethylene glycol-polyvinyl alcohol copolymer, hydroxypropyl methylcellulose phthalate or hypromellose phthalate, polyethylene glycol 15-hydroxystearate, a copolymer of methyl methacrylate and diethylaminoethylmethyl methacrylic acid ester, polymethyl acrylate-polymethyl methacrylate-polymethacrylic acid copolymer, N,N-dimethylaminoethylmethacrylate, polyvinylcaprolactam-polyvinyl acetate-polyethylene glycol graft copolymer, polybutyl methacrylate-poly N,N-dimethylaminoethyl methacrylate-polymethylmethacrylate copolymer, polyvinyl alcohol, polyethylene oxide, polyoxyethylene, hyperbranched polyesteramides, hydroxypropylmethylcellulose or hypromellose, hydroxyethylcellulose, cellulose acetate, vitamin E polyethylene glycol succinate, polydimethylsiloxane alkane, xanthan gum, polylactic acid, polylactide-polylactic acid copolymer, polycaprolactone, carnauba wax, glyceryl palmitostearate, hydrogenated castor oil, cellulose acetate butyrate, polyvinyl acetate, polyethyl acrylate-polymethylmethacrylate-polytrimethylammonium chloride ethyl methacrylate copolymer, polyethylene-polyvinyl acetate copolymer, chitosan, and a combination thereof.

In some embodiments, the materials described herein is admixed with another agent, such as an excipient and/or a plasticizer. In some embodiments, the material described herein is admixed with an excipient. In some embodiments, the excipient is selected from the group consisting of cocoa butter, polyethylene glycol (PEG), sucrose, glucose, galactose, fructose, xyloselactose, maltose, trehalose, sorbitol, mannitol, maltodextrins, raffinose, stachyose, fructo-oligosaccharides, and a combination thereof. In some embodiments, the thermoplastic material is admixed with a plasticizer. In some embodiments, the plasticizer is triethyl citrate (TEC). In some embodiments, the plasticizer is selected from the group consisting of block copolymers of polyoxyethylene-polyoxypropylene, vitamin e polyethylene glycol succinate, hydroxystearate, polyethylene glycol (such as PEG400), macrogol cetostearyl ether 12, polyoxyl 20 cetostearyl ether, polysorbate 20, polysorbate 60, polysorbate 80, acetin, acetylated triethyl citrate, tributyl citrate, tributyl o-acetylcitrate, triethyl citrate, polyoxyl 15 hydroxystearate, peg-40 hydrogenated castor oil, polyoxyl 35 castor oil, dibutyl sebacate, diethylphthalate, glycerine, methyl 4-hydroxybenzoate, glycerol, castor oil, oleic acid, tryacetin, polyalkylene glycol, and a combination thereof.

In some embodiments, the material contained in a drug dosage form is about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95% of the drug dosage form in weight.

Active Pharmaceutical Ingredient

As used herein, "active pharmaceutical ingredients (API)" refer to ingredients in pharmaceutical drugs that are biologically active. In some embodiments, the API is selected form the group consisting of: local anesthetics, antiepileptic drugs and anticonvulsants, pain management drugs, sleeping disorder drugs, anti-Alzheimer's disease drugs, analgesics, antipodagric, anti-hypertensive drugs, antiarrhythmic drugs, diuretic drugs, drugs for treating liver diseases, drugs for treating pancreatic diseases, drugs for treating gastrointestinal diseases, drugs for treating CNS diseases, antihistamine drugs, anti-allergic drugs, glucocorticoid drugs, hormone drugs and contraceptive drugs, hypoglycemic drugs, anti-osteoporosis drugs, antibiotics, sulfonamides, quinolones, and other synthetic antibacterial drugs, antituberculous drugs, antiviral drugs, anti-neoplasm drugs, immunomodulators, veterinary drugs, cosmetically active agents, nutritional agent, chemical reagents, traditional Chinese medicine and extract of traditional Chinese medicine.

In some embodiments, the API is selected from the group consisting of: (R)-folitixorin, lidocaine, 11-di-deutero-ethyllinoleate, 16-dehydro-pregnenolone, 17-beta-estradiol, 2-iminobiotin, 3,5-diiodothyropropionicacid, 5-fluoro-2-deoxycytidine, 6-mercaptopurine, edotreotide, abacavir, abalone haemocyanin, abametapir, abediterol, abemaciclib, abexinostat, abiraterone, acalabrutinib, acamprosate, acamprosatecalcium, acarbose, acebilustat, aceclidine, aceclofenac, acehytisine hydrochloride, acemannan, aceneuramic acid, acetaminophen, acetylcysteine, acetylkitasamycin, acetyl-L-carnitinehydrochloride, acetylsalicylicacid, aciclovir, acipimox, acitazanolast, acitretin, aclidinium, aclidinium bromide, acolbifene, acorafloxacin, acotiamide, acrivastine, actarit, adapalene, adapalene, adefovirdipivoxil, ademetionine, adoair, afatinib, afimoxifene, afuresertib, agomelatine, aildenafilcitrate, aladorian, alalevonadifloxacin mesylate, alarelin acetate, alatrofloxacin mesylate, albendazole, albuterol sulfate, albuterpenoids, alcaftadine, aldoxorubicin, alectinib, alendronate, alendronate sodium, alendronate sodiumhydrate, alendronic acid, alfacalcidol, alfaxalone, alfentanil, alfuzosin, alisertib, aliskiren, alisporivir, alitretinoin, allantoin, allisartanisoproxil, allopurinol, almotriptan, alogliptin, alogliptin benzoate, alosetron, alpelisib, alphaketoglutarate, alphalipoic acid, alpha-1antitrypsin, alpha-cyclodextrin-stabilized sulforaphane, alprazolam, alprostadil, alprostadil alfadex, altiratinib, altretamine, altropane, aluminum sulfate, alvimopan, alvocidib, amantadine, amantadine hydrochloride, ambrisentan, ambroxol, ambroxol hydrochloride, amcasertib, amfetamine, amfetamine polistirex, amifampridine, amifampridine phosphate, amifostine, amikacin, amiloride, aminolevulinic, aminolevulinic acid, aminolevulinic acid hydrochloride, aminopterin, amiodarone, amiselimod, amisulpride, amitifadine hydrochloride, amitriptyline, amlexanox, amlodipine, amlodipine, amlodipinebesilate, amlodipine besylate, amlodipine camsylate, amlodipine maleate, amlodipine nicotinate, amlodipine orotate, ammonium lactate, amodiaquine, amorolfine, amosulalol, amoxicillin, amoxicillin hydrate, amphetamine, amphetamine aspartate, amphetamine sulfate, amphotericinB, amphotericinB cholesterylsulfate, amphotericinB lipid complex, ampicillin sodium, ampiroxicam, amrinone, amrubicin, amtolmetinguacil, anacetrapib, anagliptin, anagrelide, anamorelin, anastrozole, ancrod, androgen, andropgrapholide, anecortave, anidulafungin, aniracetam, anistreplase, anlotinib, antazoline, antiandrogens, antineoplaston A-10, antineoplaston AS2-1, antofloxacin hydrochloride, antroquinonol, apabetalone, apalutamide, apatinib mesylate, apaziquone, apilimod mesylate, apixaban, apomorphine, apomorphine hydrochloride, apremilast, aprepitant, apricitabine, aramchol, aranidipine, arasertaconazole, arasertaconazol nitrate, arbaclofen, arbaclofen placarbil, arbekacin, arbekacin sulfate, ardeparin sodium, arformoterol, argatroban, arhalofenate, arimoclomol, aripiprazole, aripiprazole lauroxil, armodafinil, arsenictrioxide, arsenious acid, artefenomel mesylate, artemether, artemotil, artenimol, arterolane maleate, artesunate, Artiss, asapiprant, asenapine, asimadoline, astodrimer, astragaloside, asunaprevir, ataciguat, ataluren, atazanavir, atazanavir sulfate, atenolol, atomoxetine, atorvastatin, atorvastatin calcium, atorvastatin strontium, atovaquone, atrasentan, atropine, auranofin, auriclosene, avacincaptadpegol sodium, avacopan, avanafil, avatrombopag, avibactam, avibactam sodium, AvidinOx, aviptadil, avitinib, avoralstat, axelopran, axitinib, azacitidine, azacytidine, azasetron, azelaicacid, azelastine, azelastine hydrochloride, azeliragon, azelnidipine, azilsartan, azilsartan medoxomil potassium, azilsartan trimethylethanolamine, azimilide, azithromycin, azithromycin lactobionate, aztreonam, aztreonam lysine, azvudine, baclofen, bafetinib, Baicalein, baicalin, Benzalkonium Chloride (BAK)-free latanoprost, balofloxacin, balsalazide, balsalazide sodium, bambuterol, barasertib, bardoxolone methyl, baricitinib, barnidipine, basmisanil, batefenterol succinate, bazedoxifene, beclabuvir, beclometasone dipropionate, beclomethasone dipropionate, bedaquiline, bedoradrine, belinostat, beloranib, belotecan, bempedoic acid, benapenem, benazepril, bencycloquidium bromide, bendamustine, bendamustine hydrochloride, benidipine, benserazide, bentamapimod, benzalkonium chloride, benzhydrocodone, benznidazole, benzocaine, benzoylperoxide, benzydamineHCL, bepotastine, bepotastine calciumdihydrate, bepotastine salicylate, beractant, beraprost sodium, besifloxacin, besifovir, besipirdine, beta-elemene, betahistine, betaine anhydrous, betamethasone, betamethasone butyrate propionate, betamethasonedipropionate, betamethasone valerate, betamipron, betaxolol, betaxolol hydrochloride, bethanechol, betrixaban, bevacizumab, bexaglifozin, bexarotene, bezafibrate, biafungin, biapenem, bicalutamide, bicizar, bictegravir, bicyclol, bilastine, bimatoprost, binimetinib, biotin, birabresibdihydrate, biskalcitrate potassium, bismuth subgallate, bismuthyl ecabet, bisnorcymserine, bisoprolol, bisoprolol fumarate, bitespiramycin, bixalomer, bleomycin, blonanserin, boanmycin hydrochloride, boceprevir, bortezomib, bosentan, bosentan hydrate, bosutinib, bovactant, brexpiprazole, briciclib sodium, brigatinib, brilacidin, brimapitide, brimonidine, brincidofovir, brinzolamide, brivanibalaninate, brivaracetam, brivudine, brolucizumab, bromazepam, bromfenac, bromfenac sodium, bromocriptine, bronchostat, brotizolam, bryostatin-1, bucindolol, bucladesine, budesonide, budipine, buflomedil, bulaquin, bunazosin, buparlisib, bupivacaine, bupivacaine hydrochloride, buprenorphine, buprenorphine hydrochloride, bupropion, bupropion hydrochloride, burixafor, buserelin acetate, buspirone, buspirone hydrochloride, busulfan, busulfex, butenafine, butorphanol tartrate, butylphthalide, cabazitaxel, cabergoline, cabotegravir, cabozantinib S-malate, cadazolid, cadrofloxacin, caffeine, caffeine citrate, cafnea, cafusertib hydrochloride, calcipotriol, calcitriol, calcium acetate, calciumfolinate, calcium levofolinate, calcium polycarbophil, calfactant, calmangafodipir, calsurf, camicinal, camostat mesylate, camptothecin, canagliflozin, candesartan, candesartan cilexetil, canfosfamide, cangrelor, cannabidiol, capecitabine, capmatinib, capsaicin, captopril, carbamazepine, carbetocin, carbidopa, carbinoxamine, carbocysteine, carboplatin, cardidopa, carfilzomib, carglumicacid, cariprazine, carisbamate, carmustine, carotegastmethyl, carteolol, carteolol hydrochloride, carumonam, carvedilol, carvedilolphosphate, caspofungin, catechin, cebranopadol, cediranib, cefaclor, cefadroxil, cefathiamidine, cefazolin sodium pentahydrate, cefcapene, cefdinir, cefditorenpivoxil, cefepime, cefepime dihydrochloride, cefetametpivoxil hydrochloride, cefiderocol, cefilavancin, cefminox, cefoperazone, cefoperazone sodium, cefoselis, cefotaxime, cefotaxime sodium, cefotiam, cefozopran, cefpirome, cefpodoxime, cefprozil, ceftaroline, ceftaroline fosamil, ceftazidime, ceftibuten, ceftobiprole medocaril, ceftolozane sulfate, ceftriaxone, ceftriaxone sodium, cefuroxime, cefuroxime sodium, celecoxib, celgosivir, celiprolol, cellprotect, cenestin, cenicriviroc, censavudine, centanafadine, cephalosporin, ceralifimod, cerdulatinib, ceritinib, ceriumnitrate, cetilistat, cetirizine, cetraxate, cevimeline, chenodeoxycholic acid, chlocibutamine, chlorhexidine, chlormadinone acetate, chlorogenicacid, chloroquine, chloroxoquinoline, chlorpheniramine, chlorpheniramine maleate, chlorpheniramine polistirex, chlortalidone, chlorthalidone, cholecalciferol, cholic acid, choline alfoscerate, choline diepalrestat, choline fenofibrate, ciclesonide, ciclopiroxolamine, ciclosporin, cidofovir, cidoxepin, cilastatin, cilazapril, cilnidipine, cilostazol, cimetidine, cinacalcet, cinepazide maleate, cinhyaluronate sodium, cinitapride tartrate, cipargamin, ciprofibrate, ciprofloxacin, ciprofloxacin hydrochloride, ciraparantag, circadin, cisatracurium besilate, cisplatin, citalopram, citalopram hydrobromide, citicoline, citrulline, cladribine, clarithromycin, clavulanate potassium, clavulanic acid, clazosentan, clevidipine, clevudine, clindamycin, clindamycin hydrochloride, clindamycin phosphate, clioquinol, clobazam, clobetasolpropionate, clobetasolpropionatefoam, clodronic acid, clofarabine, clofazimine, clomipramine, clomipramine hydrochloride, clonazepam, clonidine, clonidine hydrochloride, clopidogrel, clopidogrel besylate, clopidogrel bisulfate, clopidogrel camsylate, clopidogrel hydrogensulfate, clopidogrel napadisilate, clopidogrel resinate, clotrimazole, clozapine, cobamamide, cobicistat, cobimetinib, cobiprostone, codeine, codeine polistirex, colchicine, colecalciferol, colesevelam, colestilan, colforsin daropate, colfosceril palmitate, colistimethate sodium, conivaptan, copanlisib, copperhistidine, cortexolone 17alpha-propionate, cositecan, crenolanib, cridanimod sodium, crisaborole, crizotinib, crofelemer, crolibulin, cromoglicic acid, cromolyn sodium, cutamesine dihydrochloride, cyanocobalamin, cyclizine lactate, cyclobenzaprine hydrochloride, cyclophosphamide, cyclophosphamide monohydrate, cyclosporin, cyproterone, cyproterone acetate, cytarabine, cytarabine ocfosfate, dabigatran etexilate, dabrafenib, daclatasvir, dacomitinib, dalbavancin, dalcetrapib, dalfampridine, dalfopristin, dalteparin sodium, danaparoid sodium, danazol, danirixin, danoprevir, dantrolene sodium, danusertib, dapaconazole, dapagliflozin, dapagliflozin propanediol, dapiprazole, dapivirine, dapoxetine, daprodustat, dapsone, darifenacin, darinaparsin, darunavir, dasabuvir, dasatinib, dasotraline, daunorubicin, decitabine, decuprate, defactinib, deferasirox, deferiprone, deferoxamine mesylate, deflazacort, deflexifol, delafloxacin, delamanid, delapril, delapril hydrochloride, delavirdine, denibulin, deoxyandrographolide, dermatansulfate, desflurane, desipramine hydrochloride, desloratadine, desmopressin, desmopressin acetate, desogestrel, desonide, desvenlafaxine, deudextromethorphan hydrobromide, deuteporfin, deuterated levodopa, deuteratedvenlafaxine, deutetrabenazine, dexamethasone, dexamethasone acetate, dexamethasone cipecilate, dexamethasone palmitate, dexamethasone sodiumphosphate, dexamfetamine, dexanabinol, dexferrum, dexketoprofen trometamol, dexlansoprazole, dexmedetomidine, dexmethylphenidate, dexpramipexole, dexrazoxane, dexsotalol, dextroamphetamine saccharate, dextroamphetamine sulfate, dextromethorphan, dextromethorphan hydrobromide, dextropropoxyphene, diacerein, diamorphine hydrochloride, dianhydrogalactitol, diazepam, diazoxidecholine, diclofenac, diclofenac potassium, diclofenac sodium, diclofenamide, dicycloplatin, didanosine, dienogest, difluprednate, digoxin, dihomogamma-linolenic acid, dihydroergocristine, dihydroergotamine, dihydroergotamine mesylate, diltiazem, diltiazem hydrochloride, dimesna, dimethyl fumarate, dimiracetam, dinoprostone, diphenylcyclopropenone, dipraglurant, dipyridamole, diquafosoltetra sodium, dirithromycin, disufenton sodium, disulfiram, dithranol, d-methadone, docarpamine, docetaxel, dociparstat, docosanol, dofetilide, dolasetron, dolutegravir, domperidone, donafenib tosylate, donepezil, donepezil hydrochloride, dopamine, doravirine, doripenem, dorzolamide, dorzolamide hydrochloride, dosmalfate, doxacurium chloride, doxazosin, doxazosin mesylate, doxepin hydrochloride, doxercalciferol, doxifluridine, doxofylline, doxorubicin, doxorubicin hydrochloride, doxycycline, doxycycline hyclate, doxylamine succinate, dronabinol, dronedarone, drospirenone, droxidopa, D-tagatose, duloxetine, duloxetine hydrochloride, dutasteride, duvelisib, ebastine, eberconazole, ebselen, ecabet, econazolenitrate, ecopipam, edaravone, edivoxetine, edonerpic maleate, edoxaban, efatutazone, efavirenz, efinaconazole, eflornithine, efonidipin hydrochloride, egualen sodium, eicosapentaenoic acid monoglycerides, elafibranor, elagolix, elamipretide, elbasvir, eldecalcitol, eleclazine, elesclomol sodium, eletriptan, eliglustattartrate, elobixibat, eltrombopag, eluxadoline dihydrochloride, elvitegravir, emdogain, emedastine, emeramide, emixustat, emodepside, empagliflozin, emricasan, emtricitabine, enalapril, enalaprilmaleate, enasidenib, encenicline, enclomifene citrate, encorafenib, endoxifen, enobosarm, enoxacin gluconate, enoxaparin sodium, enprostil, entacapone, entasobulin, entecavir, entecavir maleate, entinostat, entospletinib, entrectinib, enzalutamide, enzastaurin, epacadostat, epalrestat, eperisone, epetraborole, ephedrine sulfate, epinastine hydrochloride, epinephrine, epirubicin, epirubicin hydrochloride, episalvan, epitinib, eplerenone, epoprostenol, epristeride, eprodisate, eprosartan, eptaplatin, eravacycline, erdafitinib, erdosteine, eribulin mesylate, erlotinib, ertapenem, erteberel, ertugliflozin, erythromycin, erythromycin acistrate, erythromycin stinoprate, escitalopram, esketamine, esketamine hydrochloride, eslicarbazepine acetate, esmolol hydrochloride, esomeprazole, esomeprazole magnesium, esomeprazole strontium, esomeprazole, estetrol, estradiol, estradiol acetate, estradiol cypionate, estradiol valerate, estrodiol, estrogen, esuberaprost sodium, eszopiclone, etamicastat, ethambutol hydrochloride, ethaselen, ethinylestradiol, ethylhydrogenfumarate calcium, ethylhydrogenfumarate magnesium, ethylhydrogenfumara tezinc, ethynylestradiol, etidronicacid, etimicin sulfate, etirinotecanpegol, etizolam, etodolac, etonogestrel, etoposide, etoposide phosphate, etoricoxib, etravirine, etripamil, eupatilin, evenamide hydrochloride, everolimus, evofosfamide, evogliptin, exemestane, exendin(9-39), exeporfinium chloride, eziatiostat, ezetimibe, ezutromid, fadolmidine, fadrozole, faldaprevir, falecalcitriol, famciclovir, famitinib, famotidine, fampridine, faropenem, fasitibant chloride, fasoracetam, fasudil, fasudil hydrochloride, fasudil mesylate, favipiravir, febarbamate, febuxostat, fedovapagon, felbamate, felbinac trometamol, felodipine, femitra, fenfluramine hydrochloride, fenobam, fenofibrate, fenofibric acid, fenoldopam, fenoterol, fenretinide, fentanyl, fentanyl citrate, fenticonazole, fermagate, ferriccitrate, ferricmaltol, ferumoxytol, fesoterodine fumarate, fevipiprant, fexinidazole, fexofenadine, fibrinsealant, fibrinogen, fibrinogensealant, fidaxomicin, filanesib, filgotinib, filociclovir, fimaporfin, fimasartan, finafloxacin, finafloxacin hydrochloride, finasteride, finerenone, fingolimod, fipamezole, firtecanpegol, flecainide, fleroxacin, flibanserin, flomoxef, floxuridine, fluazolepali, fluconazole, fludarabine, flumatinib, flumazenil, flunisolide, fluocinolone acetonide, fluocinonide, fluorapacin, fluorouracil, fluoxetine, fluoxetine hydrochloride, flupirtine, flurbiprofen, flurbiprofenaxetil, flurbiprofen sodium, flurithromycin, fluticasone, fluticasone furoate, fluticasone propionate, flutrimazole, fluvastatin, fluvoxamine, folic acid, folinate, foliumginkgo, fomepizole, fonadelpar, fondaparinux sodium, foretinib, formestane, formoterol, formoterol fumarate, forodesine, fosamprenavir, fosaprepitant, fosbretabulin, fosbretabulin disodium, fosfluconazole, fosfomycin, fosfomycindi sodium, fosfomycintrometamol, fosinopril, fosinopril sodium, fosmidomycin, fosphenytoin, fospropofol, fosravuconazole, fostamatinib, fostemsavir tromethamine, fotagliptin benzoate, fotemustine, frovatriptan, fruquintinib, fudosteine, fulvestrant, funapide, furosemide, fusidic acid, gabapentin, gabapentinenacarbil, gabexate mesylate, gacyclidine, gadobutrol, gadoversetamide, gadoxetate disodium, galantamine, galeterone, galidesivir, gallium nitrate, galunisertib, gambogic acid, ganaxolone, ganciclovir, ganetespib, ganirelix acetate, garenoxacin, gatifloxacin, gatifloxacin mesylate, gedatolisib, gefitinib, gemcabene, gemcitabine, gemcitabine hydrochloride, gemfibrozil, gemifloxacin, gemigliptin, gemigliptintartaric acid, genistein, gentamicin, gentiopicrin, gepirone, gepotidacin, gestodene, gestrinone, timolol maleate, gilteritinib, gimeracil, ginsenosideC-K, ginsenosideRg3, givinostat, glasdegib, glatiramer acetate, glecaprevir, glesatinib glycolate, glibenclamide, gliclazide, glimepiride, glipizide, glufosfamide, glutamine, glutathionarsenoxide, glycerol phenylbutyrate, glycopyrronium, glycopyrronium bromide, glycopyrronium tosylate, glycyrrhizi cacid, ganglioside, golotimod, gosogliptin, granisetron, granisetron hydrochloride, grazoprevir, guaifenesin, guaimesal, guanfacine, gusperimus trihydrochloride, haemophilusinfluenzae, halobetasol propionate, halofantrine, halometasone, healon, hematoporphyrin, hemearginate, hemocoagulase acutus, heparin, Herbiron, hetrombopag, hextend, higenaminehydrochloride, histamine dihydrochloride, HPPHphotosensitizer, humanapotransferrin, humanplasminogen, huperzineA, hyaluronate sodium, hydralazine, hydrochloride, hydrochlorothiazide, hydrocodone, hydrocodone bitartrate, hydrocodone polistirex, hydrocortisone, hydrogenperoxide, hydromorphone, hydromorphone hydrochloride, hydroxocobalamin, hydroxycarbamide, hydroxychloroquine, hydroxyprogesterone caproate, hydroxysafflor yellowA, hylastan, hypericin, hypoestoxide, ibandronate, ibandronic acid, iberogastN, ibodutant, ibrutinib, ibudilast, ibuprofen, ibutilide, ibutilide fumarate, icaritin, iclaprim, icosabutate, icosapent, icosapentethyl, icosapentethylester, icotinib hydrochloride, idalopirdine, idasanutlin, idebenone, idelalisib, idoxuridine, idronoxil, ifetroban, ifetrobansodium, iguratimod, ilansoprazole, ilaprazole, iloperidone, iloprost, iloprostbetadexclathrate, imatinib, imatinibmesylate, imeglimin, imidafenacin, imidapril, imidazole salicylate, imidol hydrochloride, imigliptin dihydrochloride, imipenem, imiquimod, imisopasem manganese, imrecoxib, incadronic acid, incobotulinumtoxin, indacaterol, indacaterol maleate, indapamide, indeloxazine, Indimitecan, indinavir, indisetron, indometacin, indoramin, indotecan, indoximod, inecalcitol, infigratinib, Ingavirin, ingenolmebutate, inhaled sodium nitrite, ferric carboxymaltose, inosine, intepirdine, iodiconazole, ipatasertib dihydrochloride, ipraglifozin, ipratropium, ipratropium bromide, iptakalim, irbesartan, irinotecan, irinotecan hydrochloride, irinotecan sucrosofate, irofulven, iron isomaltoside1000, iron protein succinylate, irosustat, irsogladine maleate, isavuconazonium chloride/sulfate, isodibut, isoflurane, isoniazid, isopropylunoprostone, isosorbidedi nitrate, isosorbide mononitrate, isosteviol, isothiafludine, isotretinoin, isradipine, istaroxime, istradefylline, itacitinib, itopride hydrochloride, itraconazole, ivabradine hemisulfate, ivabradine hydrochloride, ivacaftor, ivermectin, ivosidenib, aflibercept, ixabepilone, ixazomib citrate, kallikrein, kangbeide, ketamine, ketanserin, ketoconazole, ketoprofen, ketorolac, ketorolac tromethamine, ketotifen, kevetrin, kukoamine Bmesylate, L-4-chlorokynurenine, lacidipine, lacosamide, lactitol, ladarixin, ladostigil, laflunimus, lafutidine, lamivudine, lamotrigine, landiolol, landiolol hydrochloride, laninamivir octanoate, lanoconazole, lansoprazole, lanthanum carbonate, lapatinib, laquinimod, laromustine, lasmiditan, lasofoxifene, latanoprost, latanoprostenebunod, lauflumide, ledipasvir, lefamulin, leflunomide, lemborexant, lenalidomide, lentinan, lentinansulfate, lentinanviral, lenvatinib mesylate, lercanidipine, lesinurad, leteprinim, letermovir, letrozole, leucine, leuprorelin acetate, levalbuterol, levalbuterol hydrochloride, levamisole, levamlodipine, levamlodipine besylate, levamlodipine maleate, levetiracetam, levobupivacaine, levocabastine, levocabastine hydrochloride, levocarnitine, levocetirizine dihydrochloride, levodopa, levodoxazosin mesylate, levofloxacin, levoketoconazole, levomilnacipran, levonadifloxacin arginine salt, levonorgestrel, levonorgestrel butanoate, levo-phencynonate hydrochloride, levornidazole, levorphanol, levosimendan, levothyroxine sodium, levotuss, L-glutamine, lidocaine, lifitegrast, ligustrazine hydrochloride, limaprost, linagliptin, linezolid, liothyronine, liothyronine sodium, lipobean, liposomal curcumin, lipoteichoic acid, liranaftate, lisdexamfetamine, lisinopril, lisofylline, lisuridehydrogen maleate, lithiumcitrate, lithiumsuccinate, lixivaptan, lobaplatin, lobeglitazone, lodenafil carbonate, lofexidine, lomefloxacin, lomerizine, lomerizine dihydrochloride, lomitapide, lonafarnib, lonidamine, loperamide, loperamideoxide, lopinavir, loratadine, lorazepam, lorcaserin, lorediplon, lorlatinib, L-ornithineL-aspartate, lornoxicam, losartan, losartan potassium, losmapimod, loteprednoletabonate, lovastatin, loxapine, loxoprofen, L-praziquantel, lubiprostone, lucanthone, lucerastat, lucinactant, lucitanib hydrochloride, luliconazole, lumacaftor, lumaterperone toluene sulfonate, lumefantrine, lumiracoxib, lunacalcipol, lurasidone, lurbinectedin, luseogliflozin hydrate, lusutrombopag, lysine acetylsalicylate, macimorelin, macitentan, mafenide, magnesium carbonate, magnesium isoglycyrrhizinate, mangafodipir, manidipine, manidipine dihydrochloride, mannitol, maraviroc, maribavir, marizomib, masilukast, masitinib, mavoglurant, maxacalcitol, mebendazole, mebiphon, mecamylamine, mecamylamine hydrochloride, mechlorethamine, mecobalamin, medroxyprogesterone, medroxyprogesteroneacetate, mefloquine, megestrol, megestrolacetate, meisuoshuli, melevodopa, meloxicam, melphalan, melphalanflufenamide hydrochloride, memantine, memantine hydrochloride, menadione sodium bisulfite, menatetrenone, mepacrine, mequinol, mercaptamine, mercaptamine bitartrate, mercaptamine hydrochloride, mercaptopurine, merestinib, meropenem, merotocin, mesalamine, mesalazine, metacavir, metadoxine, metamizolesodium, metaxalone, metergoline, metformin, metformin hydrochloride, methadone, methazolamide, methotrexate, methoxyflurane, methylaminolevulinate hydrochloride, methylnaltrexone bromide, methylnaltrexone, methylphenidate, methylphenidate hydrochloride, methylprednisolone, methylprednisolone aceponate, methylthioninium chloride, metirosine, metoclopramide, metoprolol, metoprolol succinate, metrifonate, metronidazole, metyrapone, mexiletine, mibefradil, miconazole, miconazole nitrate, midazolam, midazolam hydrochloride, midodrine, midostaurin, mifamurtide, mifepristone, migalastat, miglitol, miglustat, milnacipran, milrinone, miltefosine, minaprine, minocycline, minocycline hydrochloride, minodronic acid, minoxidil, mirabegron, miriplatin hydrate, mirodenafil, mirodenafil hydrochloride, mirogabalin, mirtazapine, misoprostol, mitiglinide, mitomycin, mitoxantrone, mitoxantrone hydrochloride, mivotilate, mizolastine, mizoribine, mocetinostat dihydrobromide, moclobemide, modafinil, doxycycline, modipafant, moexipril, mofezolac, molidustat, molindone hydrochloride, momelotinib, mometasone, monepantel, monoammonium glycyrrhizinate, monobenzone, monosodium alphaluminol, monoterpene perillyl alcohol, montelukast, montelukast sodium, montmorillonite, moracizine, morinidazole, morphine, morphine glucuronide, morphine pitavastatin, morphine sulfate, morphothiadine mesilate, mosapride, motolimod, moxidectin, moxifloxacin, moxifloxacin hydochloride, moxonidine, moxonidine hydrochloride, mozavaptan, muparfostat sodium, mupirocin, mycobactovir, mycophenolatemofetil, myristylnicotinate, nabilone, nabiximols, nabumetone, N-acetylcysteine, nacystelyn, nadifloxacin, nadolol, nadroparin calcium, naftifine hydrochloride, naftopidil, nalbuphine, nalbuphine sebacate, naldemedine, nalfurafine, nalmefene, naloxegol, naloxone, naloxone hydrochloride, naltrexone, naltrexone hydrochloride, naluzotan, nandrolone decanoate, napabucasin, naphazoline, naphthoquine, naproxen, naproxen sodium, naquotinib mesylate, naratriptan, narlaprevir, nasapaque, nasaruplase, nastorazepide calcium, nateglinide, navamepent, nazartinib, nebivolol, necuparanib, nedaplatin, nedocromil, nelarabine, nelfinavir, nelotanserin, nemonapride, nemonoxacin, neoandrographolide, neosaxitoxin, neostigmine methyl sulfate, nepadutant, nepafenac, nepicastat, nepolong, neramexane, neratinib, neridronic acid, netarsudil, netilmicin, netupitant, nevirapine, niacin, nicardipine, nicergoline, nicorandil, nicotiflorin, nicotine, nicotinicacid, nicousamide, nifedipine, nifekalant, nifeviroc, Nifurtimox, nifurzide, nikkomycin, nilotinib, nilutamide, nilvadipine, nimesulide, nimodipine, nimorazole, ningetinib, nintedanib, niraparib, nisoldipine, nitazoxanide, nitisinone, nitrendipine, nitricoxide, nitroglycerin, nitroglycerine, nizatidine, nokxaban, nolatrexed, nomegestrol acetate, norelgestromin, norepinephrine, norethindrone, norethindrone acetate, norethindrone enantate, norethisterone, norethisterone acetate, norfloxacin, norgestimate, noribogaine, norursodeoxycholic acid, obeticholicacid, octenidine, octohydroaminoacridine succinate, octreotide, octreotide hydrochloride, odalasvir, odanacatib, odiparcil, ofloxacin, olanzapine, olaparib, olesoxime, olieridine, olmesartan, olmesartan cilexetil, olmesartan medoxomil, olodaterol, olodaterol hydrochloride, olopatadine, olopatadine hydrochloride, olprinone, olsalazine, oltipraz, omacetaxine mepesuccinate, omadacycline, omarigliptin, omaveloxolone, ombitasvir, omecamtivmecarbil, omega-3 carboxylicacids, omeprazole, omigapil, omoconazole, onalespib, onapristone, ondansetron, ondelopran, opicapone, opipramol, methylphenidate, orcinoside, orilotimod, oritavancin, orlistat, ornithine phenylacetate, ornoprostil, ortataxel, orteronel, orthovisc, orvepitant, oseltamivir, osilodrostat, osimertinib, Osiris Phleum pratense, ospemifene, oteracil potassium, oteseconazole, oxaliplatin, oxaloacetic acid, oxandrolone, oxazepam, oxcarbazepine, oxfendazole, oxidizedglutathione sodium, oxiracetam, oxybutynin, oxybutynin hydrochloride, oxycodone, oxycodone hydrochloride, oxymetazoline, oxymetazoline hydrochloride, oxymorphone, oxytocin, ozagrel, ozagrel hydrochloride, ozagrelsodium, ozanimod, ozenoxacin, paclitaxel, paclitaxel poliglumex, pacritinib, palbociclib, paliperidone, paliperidone palmitate, palmidrol, palonosetron, palovarotene, pamidronate disodium, pancrelipase, panipenem, panobinostat, pantoprazole, paracetamol, parecoxib, paricalcitol, paritaprevir, parnaparin sodium, parogrelil, paromomycin, paroxetine, paroxetine hydrochloride hemihydrate, paroxetine mesylate, patiromer calcium, patupilone, pazopanib, pazufloxacin, pazufloxacin mesylate, pefcalcitol, peficitinib, pegylatedapo-filgrastim, pelubiprofen, pemafibrate, pemetrexed disodium, pemirolast, pemirolast potassium, pemirolast sodium, penciclovir, penehyclidine hydrochloride, pentamidine, pentetate calcium trisodium, pentetatezinc trisodium, pentetrazol, pentosan polysulfate sodium, pentostatin, pentoxifylline, peramivir, perampanel, perchlozone, peretinoin, perflenapent, perflubronemulsion, perfluorooctyl bromide, pergolide, perhexiline maleate, perifosine, perindopril, perindopril arginine, perospirone, pevonedistat, pexidartinib, PhagoBioDerm, phenchlobenpyrrone, phenethyl isothiocyanate, phenoxybenzamine hydrochloride, phentermine, phentermine hydrochloride, phentolamine mesylate, phenylbutyrate, phenylephrine, phenylephrine hydrochloride, phenytoin, phosphazid, pibrentasvir, picibanil, picroliv, picropodophyllin, pidotimod, pilocarpine, pilocarpine hydrochloride, pilsicainide, pimasertib hydrochloride, pimavanserin, pimecrolimus, pimobendan, pinocembrin, pinometostat, pioglitazone, pioglitazone hydrochloride, pipamperone, pipecuronium, piperacillin, piperacillin sodium, piperaquine, piperaquine phosphate, piperidone hydrochloridum, piperine, piperphentonamine, piracetam, pirarubicin, pirfenidone, pirmenol, piromelatine, pirotinib, piroxicam, piroxicambetadex, pitavastatin, pitavastatin calcium, pitolisant, pixantrone, plazomicin, pleconaril, plerixafor, plinabulin, pocapavir, hydromorphone, podofilox, polaprezinc, polmacoxib, polydatin, polyoxidonium, pomaglumetad methionil, pomalidomide, ponatinib, ponesimod, porfimer sodium, posaconazole, posiphen, potassium bicarbonate, potassium citrate, potassium clavulanate, poziotinib, pracinostat, pradefovir, pralatrexate, pramipexole, pramiracetam, pranlukast, pranlukast hydrate, prasterone, prasugrel, pravastatin, prazosin, prednimustine, prednisolone, prednisoloneacetate, prednisolone sodiumphosphate, prednisone, pregabalin, prempro, presatovir, pretomanid, previdersin, prexasertib, pridopidine, prilocaine, pritelivir, procaterol hydrochloride, prochlorperazine, prochlorperazinemaleate, profezyme, progesterone, progestogen, progestogendienogest, proguanil, promethazine, promitil, propafenone, propagermanium, propofol, propranolol, propranolol hydrochloride, prostat, proxodolol, prucalopride, prulifloxacin, prurisol, prussianblueinsoluble, pseudoephedrine, pseudoephedrine hydrochloride, puerarin, puquitinib mesylate, pyrazinamide, pyridoxamine dihydrochloride, pyridoxine hydrochloride, pyrimethamine, pyronaridine, pyrroltinibmaleate, quazepam, quetiapine fumarate, quetiapine, quinagolide hydrochloride, quinapril hydrochloride, quinidine sulfate, quinine sulfate, quinupristin, quisinostat, quizartinibdi hydrochloride, rabeprazole, rabeprazolesodium, rabeximod, racecadotril, radezolid, radotinib, ralfinamide, ralimetinib, ralinepag, raloxifene, raltegravir, raltitrexed, ramatroban, ramelteon, ramipril, ramosetron, ranitidine, ranitidine bismuth citrate, ranolazine, rasagiline, ravidasvir hydrochloride, raxatrigine, rebamipide, rebastinib, reboxetine, reboxetine mesylate, recilisib sodium, recoflavone, redaporfin, ibuprofen, naproxen, glycopyrronium bromide, refametinib, regorafenib, relebactam, relenopride, relugolix, remeglurant, remifentanil, remifentanil hydrochloride, remimazolam, remimazolam tosylate, remogliflozin etabonate, repaglinide, reparixin, repirinast, amlexanox, chlorcyclizine hydrochloride, bucillamine, guanabenz, mazindol, naltrexone, nitisinone, ondansetron, phacetoperane, retigabine, rosiglitazone, sodium phenylbutyrate, resiniferatoxin, resiquimod, resminostat, resveratrol, retagliptin, retapamulin, retigabine, retinoicacid, retosiban, revaprazan, revefenacin, reviparin sodium, rhein, rhenium-186 etidronate, ribavirin, ribociclib, ricolinostat, ridinilazole, ridostin, rifabutin, rifampicin, rifamycin, rifapentine, rifaximin, rigosertib sodium, rilapladib, rilpivirine, rilpivirine hydrochloride, riluzole, rimantadine, rimeporide, rimexolone, riociguat, ripasudil hydrochloride hydrate, risedronate sodium, risperidone, ritonavir, rivaroxaban, rivastigmine, rivipansel sodium, rizatriptan, rizatriptan benzoate, rmulation, rociletinib, roflumilast, rokitamycin, rolapitant, romurtide, ronacaleret, roneparstat, ronopterin, ropinirole, ropinirole hydrochloride, ropivacaine, rosebengal sodium, rosiglitazone, rosiglitazone maleate, rosiglitazone sodium, rostafuroxin, rosuvastatin, rosuvastatin calcium, rotigotine, rovatirelin, roxadustat, roxithromycin, rubitecan, rucaparib phosphate, rufinamide, rufloxacin, rupatadine, ruxolitinib, S-(-)-ornidazole phosphate disodium, sabarubicin, sacubitril, safinamide, salbutamol, salbutamol sulfate, salicyclic acid, salmeterol, salmeterol xinafoate, salubrinal, salvicine, samarium (153Sm) lexidronam, samidorphan, S-amlodipine nicotinate, sapacitabine, sapropterin, sapropterin dihydrochloride, saquinavir, saracatinib, sarecycline, saroglitazar, sarpogrelate hydrochloride, savolitinib, saxagliptin, scopolamine, scorpionvenom, omega-3polyunsaturated fatty acid, secnidazole, segesterone acetate, selegiline, selegiline hydrochloride, selepressin, selexipag, seliciclib, selinexor, selisistat, selumetinib, selurampanel, sepranolone, seratrodast, serlopitant, sertaconazole, sertaconazole nitrate, sertindole, sertraline, sertraline hydrochloride, setipiprant, sevelamer carbonate, sevelamer hydrochloride, seviteronel, sevoflurane, sevuparin sodium, sibutramine maleate, sibutramine mesylate, sildenafil, sildenafil citrate, silibinin dihydrogen succinate, silmitasertib, silodosin, silver sulfadiazine, simeprevir, simmitecan hydrochloride, simotinib hydrochloride, simvastatin, sinotecean, siponimod, sirolimus, sitafloxacin, sitagliptin, sitagliptinphosphate, sivelestat, sizofiran, smilagenin, S-modafinil, sobuzoxane, sodium aescinate, sodium ascorbate, sodium benzoate, sodium bicarbonate, sodium chromoglycate, sodium ferricgluconate complex, sodium glycididazole, sodium gualenate, sodium hyaluronate, sodium ibandronate, sodium nitrate, sodium nitrite, sodium oxybate, sodium phenylacetate, sodium phenylbutyrate, sodium polysulthionate, sodium prasteronesulfate, sodium pyruvate, sodium taurocholate, sodium thiosulfate, sodium zirconiumcyclosilicate, sofosbuvir, sofpironium bromide, solabegron, solifenacin, solithromycin, sonidegib, sonolisib, sophocarpine, sophoridine hydrochloride, sorafenib, sorbitol, sotagliflozin, sotirimod, sotrastaurin, sotylize, sovaprevir, sparfloxacin, sparsentan, spebrutinib, spirapril, spironolactone, squalamine, stannsoporfin, stavudine, S-tenatoprazole, stepronin, stiripentol, streptozocin, strontium malonate, strontium ranelate, succinic acid, sucralfate, sucroferric oxyhydroxide, sufentanil, suftalanzinc, sugammadex, sulbactam, sulbactam sodium, sulcardine sulfate, sulfamethoxypyrazine, sulfasalazine, sulfatinib, sulfonylurea, sulforaphane, sulfotanshinone sodium, sulindac, sulodexide, sulphamethoxazole, sulthiame, sumatriptan, sumatriptan succinate, sunitinib, sunstone, suplasyn, suplatast tosilate, suramin sodium, verapamil hydrochloride, rilpivirine, sutezolid, suvorexant, tacalcitol, tacrine, tacrolimus, tadalafil, tafamidis, tafenoquine, tafluprost, tafoxiparin sodium, taladegib, talaporfin, talazoparib, talipexole, taltirelin, tamibarotene, tamoxifen, tamsulosin, tamsulosin hydrochloride, tandospirone, tanespimycin, tapentadol, tarafenacin, tarenflurbil, tarloxotinib bromide, taselisib, tasimelteon, tasquinimod, tavaborole, tavilermide, tazarotene, tazemetostat, tazobactam, tazobactam sodium, tebipenem pivoxil, tecarfarin, tecovirimat, tectorigenin sodiumsulfonate, tedisamil, tedizolid phosphate, tefinostat, tegafur, tegaserod, teicoplanin, telaprevir, telapristone acetate, telatinib, telbivudine, telithromycin, telmisartan, telotristatetiprate, temanogrel, temocapril, temoporfin, temozolomide, temsirolimus, tenalisib, tenapanor, teneligliptin, tenofovir, tenofoviralafenamide, tenofovirdipivoxil fumarate, tenofovir disoproxil aspartate, tenofovir disoproxil fumarate, tenoxicam, tepotinib, teprenone, terameprocol, terazosin, terbinafine, terbinafine hydrochloride, terguride, teriflunomide, tesevatinib, tesofensine, testosterone, testosterone undecanoate, tetrabenazine, tetracaine, tetracaine hydrochloride, tetrahydrocannabidiol, tetrathiomolybdate, tetryzoline, tezacaftor, thalidomide, theliatinib, theophylline, therapeutic, thiazide, thienorphine hydrochloride, thiotepa, thrombin, thromboreductin, thyroxine, tiagabine, tianeptine, tibolone, ticagrelor, ticlopidine, tigecycline, tiludronatedi sodium, timolol, timolol maleate, tindamax, tinidazole, tinzaparin sodium, tioconazole, tiopronin, tiotropium bromide, tiotropium bromide monohydrate, tipelukast, tipepidine hibenzate, tipifarnib, tipiracil hydrochloride, tipranavir, tirapazamine, tirasemtiv, tirilazad, tirofiban, tirofiban hydrochloride, tivantinib, tivozanib, tizanidine, tobramycin, tocofersolan, tocoretinate, tofacitinib, tofogliflozin, tolcapone, tolimidone, tolperisone, tolterodine, tolterodine tartrate, tolvaptan, tonabersat, topiramate, topiroxostat, topotecan, topotecan hydrochloride, torasemide, toreforant, toremifene, tosedostat, tosufloxacin, totrombopag, tozadenant, trabectedin, trabodenoson, tradipitant, tramadol, tramadol hydrochloride, trametinib, trandolapril, tranexamic acid, tranilast, transcrocetinate-sodium, transepithelial riboflavin, trantinterol hydrochloride, travoprost, trazodone, trehalose, trelagliptin succinate, treosulfan, treprostinil, treprostinil diolamine, tretinoin, triamcinolone acetonide, triapine, triazolam, tribendimidine, trichlormethiazide, triciribine, triclabendazole, triclocarban, trientine hydrochloride, trifarotene, trifluridine, triflusal, triheptanoin, trilostane, trimebutine3-thiocarbamoyl-benzenesulfonate, trimebutine tosylate, trimegestone, trimethoprim, trimetrexate, trinitrate, tripotassium dicitratobismuthate, trofinetide, tropicamide, tropisetron, trospiumchloride, trovafloxacin, troxipide, tucatinib, tulobuterol, tylerdipinehydrochloride, ubenimex, ubidecarenone, ubrogepant, udenafil, ulinastatin, ulipristal, ulixertinib, ulobetasol, umeclidinium, umeclidinium bromide, upamostat, uprosertib, uracil, urapidil, uridinetriacetate, uroacitides, ursodeoxycholic acid, ursolicacid, vaborbactam, vadadustat, valaciclovir, valaciclovir hydrochloride, valbenazine, valdecoxib, valganciclovir, valomaciclovir stearate, valproic acid, valrubicin, valsartan, valsartan trisodium hemipentahydrate, vancomycin, vancomycin hydrochloride, vandetanib, vaniprevir, vanoxerine, vapendavir, vardenafil hydrochloride, varenicline, varithena, varlitinib, vatiquinone, vavelta, veliparib, velpatasvir, velusetrag, vemurafenib, venetoclax, venlafaxine, venlafaxine hydrochloride, vepoloxamer, verapamil, verapamil hydrochloride, verdinexor, veregen, vericiguat, verinurad, vernakalant, vernakalant hydrochloride, verosudil, verteporfin, verubecestat, verubulin, vesatolimod, vesnarinone, vibegron, vicagrel, vigabatrin, vilanterol, vilanterol trifenatate, vilaprisan, vilazodone, vildagliptin, vincristine sulfate, vinflunine, vinorelbine, vinpocetine, vintafolide, viralym-C, vismodegib, vistusertib, vitamin E nicotinicate, vizomitin, voglibose, volasertib, volixibat potassium ethanolate hydrate, vonoprazan fumarate, vorapaxar, voriconazole, vorinostat, vortioxetine, vortioxetine hydrobromide, vosaroxin, voxilaprevir, warfarin, xemilofiban, yimitasvir, yonkenafil, zabofloxacin, zafirlukast, zalcitabine, zaleplon, zaltoprofen, zamicastat, zanamivir, zemiStatin, Z-endoxifen hydrochloride, zibotentan, zidebactam, zidovudine, zileuton, zincacetate, zinostatin stimalamer, ziprasidone, zofenopril, zogenix, zoledronate D,L-lysinemonohydrate, zoledronate disodium, zoledronic acid, zoliflodacin, zolmitriptan, zolpidem, zolpidem tartrate, zonisamide, zopiclone, zotepine, zucapsaicin, zuclopenthixol, and zuretinol acetate.

In certain embodiments, traditional Chinese medicine is selected from the group consisting of Abelmoschi Corolla, Abri Herba, Abutili Semen, Acanthopanacis Cortex Acanthopanacis Senticosi Radix Et Rhizoma Seu Caulis, Acanthopanax Extract, Achilleae Herba, Achyranthis Bidentatae Radix, Aconiti Kusnezoffii Folium, Aconiti Kusnezoffii Radix Cocta, Aconiti Kusnezoffii Radix, Aconiti Lateralis Radix Praeparata, Aconiti Radix Cocta, Aconiti Radix, Acori Calami Rhizoma, Acori Tatarinowii Rhizoma, Adenophorae Radix, Aesculi Semen, Agkistrodon, Agrimoniae Herba, Ailanthi Cortex, Ajugae Herba, Akebiae Caulis, Akebiae Fructus, Albiziae Cortex, Albiziae Flos, Alismatis Rhizoma, Allii Macrostemonis Bulbus, Allii Sativi Bulbus, Allii Tuberosi Semen, Aloe, Alpiniae Katsumadai Semen, Alpiniae Officinarum Rhizoma, Alpiniae Oxyphyllae Fructus, Alumen, Amomi Fructus Rotundus, Amomi Fructus, Ampelopsis Radix, Andrographis Herba, Andrographolides, Anemarrhenae Rhizoma, Anemones Raddeanae Rhizoma, Angelicae Dahuricae Radix, Angelicae Pubescentis Radix, Angelicae Sinensis Radix, Anisi Stellati Fructus, Apocyni Veneti Folium, Aquilariae Lignum Resinatum, Arcae Concha, Arctii Fructus, Ardisiae Crenatae Radix, Ardisiae Japonicae Herba, Arecae Pericarpium, Arecae Semen Tostum, Arecae Semen, Arisaema Cum Bil, Arisaematis Rhizoma Preparatum, Arisaematis Rhizoma, Aristolochiae Fructus, Aristolochiae Herba, Armeniacae Semen Amarum, Arnebiae Radix, Artemisiae Annuae Herba, Artemisiae Argyi Folium, Artemisiae Scopariae Herba, Asari Radix Et Rhizoma, Asiatic Moonseed Root Extract, Asini Corii Colla, Asparagi Radix, Aspongopus, Asteris Radix Et Rhizoma, Astragali Complanati Semen, Astragali Radix Praeparata Cum Melle, Astragali Radix, Atractylodis Macrocephalae Rhizoma, Atractylodis Rhizoma, Aucklandiae Radix, Aurantii Fructus Immaturus, Aurantii Fructus, Bambusae Caulis In Taenias, Bambusae Concretio Silicea, Baphicacanthis Cusiae Rhizoma Et Radix, Belamcandae Rhizoma, Belladonna Extract, Belladonna Liquid Extract, Belladonnae Herba, Benincasae Exocarpium, Benzoinum, Berberidis Radix, Bergeniae Rhizoma, Bergenin, Bistortae Rhizoma, Bletillae Rhizoma, Bolbostemmatis Rhizoma, Bombyx Batryticatus, Borneolum Syntheticum, Borneolum, Bovis Calculus Artifactus, Bovis Calculus Sativus, Bovis Calculus, Breviscapine, Broussonetiae Fructus, Bruceae Fructus, Bubali Cornu, Buddlejae Flos, Bufonis Venenum, Bungarus Parvus, Bupleuri Radix, Calamina, Callicarpae Caulis Et Folium, Callicarpae Formosanae Folium, Callicarpae Macrophyllae Folium, Calomelas, Campsis Flos, Canarii Fructus, Canavaliae Semen, Cannabis Fructus, Capsici Fructus, Carotae Fructus, Carpesii Fructus, Carthami Flos, Caryophylli Flos, Caryophylli Fructus, Cassiae Semen, Castor Oil, Catechu, Celosiae Cristatae Flos, Celosiae Semen, Centella Total Glucosides, Centellae Herba, Centipedae Herba, Cera Chinensis, Cera Flava, Cervi Cornu Degelatinatum, Cervi Cornu Pantotrichum, Cervi Cornu, Cervi Cornus Colla, Chaenomelis Fructus, Changii Radix, Chebulae Fructus Immaturus, Chebulae Fructus, Chelidonii Herba, Chinese Angelica Liquid Extract, Chloriti Lapis, Choerospondiatis Fructus, Chrysanthemi Flos, Chrysanthemi Indici Flos, Chuanxiong Rhizoma, Cibotii Rhizoma, Cicadae Periostracum, Cichorii Herba, Cichorii Radix, Cimicifugae Rhizoma, Cinnabaris, Cinnamomi Cortex, Cinnamomi Ramulus, Cinnamon Oil, Cirsii Herba, Cirsii Japonici Herba Carbonisata, Cirsii Japonici Herba, Cissampelotis Herba, Cistanches Herba, Citri Exocarpium Rubrum, Citri Fructus, Citri Grandis Exocarpium, Citri Reticulatae Pericarpium Viride, Citri Reticulatae Pericarpium, Citri Reticulatae Semen, Citri Sarcodactylis Fructus, Clematidis Armandii Caulis, Clematidis Radix Et Rhizoma, Clinopodii Herba, Cnidii Fructus, Codonopsis Radix, Coicis Semen, Commelinae Herba, Conyzae Herba, Coptidis Rhizoma, Cordyceps, Corni Fructus, Corydalis Bungeanae Herba, Corydalis Decumbentis Rhizoma, Corydalis Rhizoma, Crataegi Folium, Crataegi Fructus, Cremastrae Pseudobulbus, Pleiones Pseudobulbus, Crinis Carbonisatus, Croci Stigma, Crotonis Fructus, Crotonis Semen Pulveratum, Curculiginis Rhizoma, Curcumae Longae Rhizoma, Curcumae Radix, Curcumae Rhizoma, Cuscutae Semen, Cyathulae Radix, Cyclovirobuxine, Cynanchi Atrati Radix Et Rhizoma, Cynanchi Paniculati Radix Et Rhizoma, Cynanchi Stauntonii Rhizoma Et Radix, Cynomorii Herba, Cyperi Rhizoma, Dahurian Rhododendron Leaf Oil, Dalbergiae Odoriferae Lignum, Daturae Flos, Dendrobii Caulis, Dendrobii Officinalis Caulis, Descurainiae Semenlepidii Semen, Desmodii Styracifolii Herba, Dianthi Herba, Dichroae Radix, Dictamni Cortex, Dioscorea Panthaicae Rhizoma, Dioscoreae Hypoglaucae Rhizoma, Dioscoreae Nipponicae Rhizoma, Dioscoreae Rhizoma, Dioscoreae Spongiosae Rhizoma, Dipsaci Radix, Draconis Sanguis, Drynariae Rhizoma, Dryopteridis Crassirhizomatis Rhizoma Carbonisatum, Dryopteridis Crassirhizomatis Rhizoma, Echinopsis Radix, Ecliptae Herba, Entadae Semen, Entianae Rhodanthae Herba, Ephedrae Herba, Ephedrae Radix Et Rhizoma, Epimedii Folium, Epimedii Wushanensis Folium, Equiseti Hiemalis Herba, Erigerontis Herba, Eriobotryae Folium, Eriocauli Flos, Erodii Herba Geranii Herba, Erycibes Caulis, Eucalyptus Oil, Eucommiae Cortex, Eucommiae Folium, Euodiae Fructus, Eupatorii Herba, Eupatorii Lindleyani Herba, Euphorbiae Ebracteolatae Radix, Euphorbiae Hirtae Herba, Euphorbiae Humifusae Herba, Euphorbiae Pekinensis Radix, Euphorbiae Semen Pulveratum, Euphorbiae Semen, Eupolyphaga Steleophaga, Euryales Semen, Fagopyri Dibotryis Rhizoma, Farfarae Flos, Ferulae Resina, Fibraureae Caulis, Fibriuretinin, Fluoritum, Foeniculi Fructus, Forsythiae Fructus, Fraxini Cortex, Fritillariae Cirrhosae Bulbus, Fritillariae Hupehensis Bulbus, Fritillariae Pallidiflorae Bulbus, Fritillariae Thunbergii Bulbus, Fritillariae Ussuriensis Bulbus, Galangae Fructus, Galla Chinensis, Galli Gigerii Endothelium Corneum, Ganoderma, Capillary Wormwood Extract, GardeniaeFructus Praeparatus, Gardeniae Fructus, Gastrodiae Rhizoma, Gecko, Gei Herba, Gendarussae Herba, Genkwa Flos, Gentianae Macrophyllae Radix, Gentianae Radix Et Rhizoma, Ginger Liquid Extract, Ginkgo Folium, Ginkgo Leaves Extract, Ginkgo Semen, Ginseng Folium, Ginseng Radix Et Rhizoma Rubra, Ginseng Radix Et Rhizoma, Glabrous Sarcandra Extract, Glechomae Herba, Gleditsiae Fructus Abnormalis, Gleditsiae Sinensis Fructus, Gleditsiae Spina, Glehniae Radix, Glycyrrhizae Radix Et Rhizoma Praeparata Cum Melle, Glycyrrhizae Radix Et Rhizoma, Gossampini Flos, Granati Pericarpium, Gypsum Fibrosum, Gypsum Ustum, Haematitum, Haliotidis Concha, Halitum, Halloysitum Rubrum, Hawthorn Leave Extract, Hedysari Radix Praeparata Cum Melle, Hedysari Radix, Hibisci Mutabilis Folium, Hippocampus, Hippophae Fructus, Hirudo, Homalomenae Rhizoma, Hordei Fructus Germinatus, Houttuyniae Herba, Hydrargyri Oxydum Rubrum, Hyoscyami Semen, Hyperici Perforati Herba, Ilicis Chinensis Folium, Ilicis Cornutae Folium, Ilicis Rotundae Cortex, Ulicii Cortex, Impatientis Semen, Imperatae Rhizoma, Indigo Naturalis, Inulae Flos, Inulae Herba, Inulae Radix, Iridis Tectori Rhizoma, Isatidis Folium, Isatidis Radix, Juglandis Semen, Jujubae Fructus, Junci Medulla, Kadsurae Caulis, Kaempferiae Rhizoma, Kaki Calyx, Kansui Radix, Knoxiae Radix, Kochiae Fructus, Lablab Semen Album, Laggerae Herba, Lagotidis Herba, Laminariae Thallus Eckloniae Thallus, Lamiophlomis Herba, Lasiosphaera Calvatia, Leonuri Fructus, Leonuri Herba, Leonurus Liquid Extract, Licorice Extract, Licorice Liquid Extract, Ligustici Rhizoma Et Radix, Ligustri Lucidi Fructus, Lilii Bulbus, Limonitum, Linderae Radix, Lini Semen, Liquidambaris Fructus, Liquidambaris Resina, Liriopes Radix, Litchi Semen, Litseae Fructus, Lobeliae Chinensis Herba, Longan Arillus, Lonicerae Flos, Lonicerae Japonicae Caulis, Lonicerae Japonicae Flos, Lophatheri Herba, Luffae Fructus Retinervus, Lycii Cortex, Lycii Fructus, Lycopi Herba, Lycopodii Herba, Lygodii Spora, Lysimachiae Herba, Lysionoti Herba, /-Borneolum, /-Menthol, Magnetitum, Magnoliae Flos, Magnoliae Officinalis Cortex, Magnoliae Officinalis Flos, Mahoniae Caulis, Malvae Fructus, Manis Squama, Mantidis OOTheca, Margarita, Margaritifera Concha, Marsdeniae Tenacissimae Caulis, Mel, Melanteritum, Meliae Cortex, Melo Semen, Menispermi Rhizoma, Menthae Haplocalycis Herba, Meretricis Concha, Cyclinae Concha, Micae Lapis Aureus, Microctis Folium, Mirabilitum Praeparatum, Momordicae Semen, Mori Cortex, Mori Folium, Mori Fructus, Mori Ramulus, Morindae Officinalis Radix, Moschus, Moslae Herba, Moutan Cortex, Mume Flos, Mume Fructus, Murrayae Folium Et Cacumen, Mylabris, Myristicae Semen, Myrrha, Nardostachyos Radix Et Rhizoma, Natrii Sulfas Exsiccatus, Natrii Sulfas, Nelumbinis Folium, Nelumbinis Plumula, Nelumbinis Receptaculum, Nelumbinis Rhizomatis Nodus, Nelumbinis Semen, Nelumbinis Stamen, Nigellae Semen, Notoginseng Radix Et Rhizoma, Notoginseng Total Saponins, Notoginseng Triol Saponins, Notopterygii Rhizoma Et Radix, Ocimum Gratissimum Oil, Olibanum, Omphalia, Ophicalcitum, Ophiopogonis Radix, Orostachyis Fimbriatae Herba, Oroxyli Semen, Oryzae Fructus Germinatus, Osmundae Rhizoma, Ostreae Concha, Paeoniae Radix Alba, Paeoniae Radix Rubra, Panacis Japonici Rhizoma, Panacis Majoris Rhizoma, Panacis Quinquefolii Radix, Papaveris Pericarpium SI, Paridis Rhizoma, Patchouli Oil, Pegaeophyti Radix Et Rhizoma, Peppermint Oil, Perillae Caulis, Perillae Folium, Perillae Fructus, Periplocae Cortex, Persicae Ramulus, Persicae Semen, Peucedani Decursivi Radix, Peucedani Radix, Pharbitidis Semen, Phellodendri Amurensis Cortex, Phellodendri Chinensis Cortex, Pheretima, Phragmitis Rhizoma, Phyllanthi Fructus, Physalis Calyx Seu Fructus, Physochlainae Radix, Phytolaccae Radix, Picrasmae Ramulus Et Folium, Picriae Herba, Picrorhizae Rhizoma, Pinelliae Rhizoma Praeparatum Cum Alumine, Pinelliae Rhizoma Praeparatum Cum Zingibere Et Alumine, Pinelliae Rhizoma Praeparatum, Pinelliae Rhizoma, Pini Lignum Nodi, Pini Pollen, Piperis Fructus, Piperis Kadsurae Caulis, Piperis Longi Fructus, Plantaginis Herba, Plantaginis Semen, Platycladi Cacumen, Platycladi Semen, Platycodonis Radix, Pogostemonis Herba, Polygala Liquid Extract, Polygalae Japonicae Herba, Polygalae Radix, Polygonati Odorati Rhizoma, Polygonati Rhizoma, Polygoni Avicularis Herba, Polygoni Cuspidati Rhizoma Et Radix, Polygoni Multiflori Caulis, Polygoni Multiflori Radix Praeparata, Polygoni Multiflori Radix, Polygoni Orientalis Fructus, Polygoni Perfoliati Herba, Polygoni Tinctorii Folium, Polyporus, Poria, Portae Cutis, Portulacae Herba, Potentillae Chinensis Herba, Potentillae Discoloris Herba, Powdered Buffalo Horn Extract, Prinsepiae Nux, Propolis, Prunellae Spica, Pruni Semen, Psammosilenes Radix, Pseudolaricis Cortex, Pseudostellariae Radix, Psoraleae Fructus, Pterocephali Herba, Puerariae Lobatae Radix, Puerariae Thomsonii Radix, Pulsatillae Radix, Pyritum, Pyrolae Herba, Pyrrosiae Folium, Quisqualis Fructus, Rabdosiae Rubescentis Herba, Ranae Oviductus, Ranunculi Ternati Radix, Raphani Semen, Realgar, Rehmanniae Radix Praeparata, Rehmanniae Radix, Rhapontici Radix, Rhei Radix Et Rhizoma, Rhodiolae Crenulatae Radix Et Rhizoma, Rhododendri Daurici Folium, Rhododendri Mollis Flos, Rhubarb Extract, Rhubarb Liquid Extract, Ricini Semen, Rosae Chinensis Flos, Rosae Laevigatae Fructus, Rosae Rugosae Flos, Rubi Fructus, Rubiae Radix Et Rhizoma, Saigae Tataricae Cornu, Salvia Total Phenolic Acids, Salviae Miltiorrhizae Radix Et Rhizoma, Sanguisorbae Radix, Santali Albi Lignum, Saposhnikoviae Radix, Sappan Lignum, Sarcandrae Herba, Sargassum, Sargentodoxae Caulis, Sauropi Folium, Saururi Herba, Saussureae Involucratae Herba, Schisandrae Chinensis Fructus, Schisandrae Sphenantherae Fructus, Schizonepetae Herba Carbonisata, Schizonepetae Herba, Schizonepetae Spica Carbonisata, Schizonepetae Spica, Scolopendra, Scorpio, Scrophulariae Radix, Scutellaria Extract, Scutellariae Barbatae Herba, Scutellariae Radix, Sedi Herba, Selaginellae Herba, Semiaquilegiae Radix, Senecionis Scandentis Hebra, Sennae Folium, Sepiae Endoconcha, Serpentis Periostracum, Sesame Oil, Sesami Semen Nigrum, Setariae Fructus Germinatus, Siegesbeckiae Herba, Silybi Fructus, Sinapis Semen, Sinomenii Caulis, Sinopodophylli Fructus, Siphonostegiae Herba, Siraitiae Fructus, Smilacis Chinae Rhizoma, Smilacis Glabrae Rhizoma, Sojae Semen Germinatum, Sojae Semen Nigrum, Sojae Semen Praeparatum, Solidaginis Herba, Sophorae Flavescentis Radix, Sophorae Flos, Sophorae Fructus, Sophorae Tonkinensis Radix Et Rhizoma, Sparganii Rhizoma, Spatholobi Caulis, Spiceleaf Kernel Oil, Spirodelae Herba, Stachyuri Medulla Helwingiae Medulla, Stalactitum, Star Anise Oil, Stauntoniae Caulis Et Folium, Stellariae Radix, Stemonae Radix, Stephaniae Tetrandrae Radix, Sterculiae Lychnophorae Semen, Strychni Semen Pulveratum, Strychni Semen, Styrax, Suis Fellis Pulvis, Sulfur, Swertiae Herba, Swertiae Mileensis Herba, Syngnathus, Syringae Cortex, Talci Pulvis, Talcum, Tamaricis Cacumen, Tanshinones, Taraxaci Herba, Taxilli Herba, Tea-Seed Oil, Terminaliae Belliricae Fructus, Testudinis Carapacis Et Plastri Colla, Testudinis Carapax Et Plastrum, Tetrapanacis Medulla, Thlaspi Herba, Thunberg Fritillary Liquid Extract, Tinosporae Radix, Toatal Ginsenoside Of Ginseng Stems And Leaves, Toosendan Fructus, Torreyae Semen, Total Ginsenoside Ginseng Root, Toxicodendri Resina, Trachelospermi Caulis Et Folium, Trachycarpi Petiolus, Tribuli Fructus, Trichosanthis Fructus, Trichosanthis Pericarpium, Trichosanthis Radix, Trichosanthis Semen Tostum, Trichosanthis Semen, Trigonellae Semen, Trionycis Carapax, Tsaoko Fructus, Turpentine Oil, Turpiniae Folium, Typhae Pollen, Typhonii Rhizoma, Uncariae Ramulus Cum Uncis, Vaccariae Semen, Valerianae Jatamansi Rhizoma Et Radix, Verbenae Herba, Vespae Nidus, Vignae Semen, Violae Herba, Visci Herba, Vitex Oil, Viticis Fructus, Viticis Negundo Folium, Vladimiriae Radix, Weeping Forsythia Extract, Wenyujin Rhizoma Concisum, Xanthii Fructus, Zanthoxyli Pericarpium, Zanthoxyli Radix, Zaocys, Zedoary Turmeric Oil, Zingiberis Rhizoma Praeparatum, Zingiberis Rhizoma Recens, Zingiberis Rhizoma, Ziziphi Spinosae Semen.

In some embodiments, the amount of an API in a drug dosage form is about 1 mg to about 60 mg, such as any of about 1.75 mg to about 60 mg, about 1.75 mg to about 20 mg, or about 2.5 mg to about 50 mg. In some embodiments, the amount of an API in a drug dosage form is less than about 60 mg, such as less than about any of 55 mg, 50 mg, 45 mg, 40 mg, 35 mg, 30 mg, 25 mg, 20 mg, 15 mg, 14 mg, 13 mg, 12 mg, 11 mg, 10 mg, 9 mg, 8 mg, 7 mg, 6 mg, 5 mg, 4.5 mg, 4 mg, 3.5 mg, 3 mg, 2.5 mg, 2 mg, 1.75 mg, or 1.5 mg. In some embodiments, the amount of an API in a drug dosage form is greater than about 1 mg, such as greater than about any of 1.5 mg, 1.75 mg, 2 mg, 2.5 mg, 3 mg, 3.5 mg, 4 mg, 4.5 mg, 5 mg, 6 mg, 7 mg, 8 mg, 9 mg, 10 mg, 11 mg, 12 mg, 13 mg, 14 mg, 15 mg, 20 mg, 25 mg, 30 mg, 35 mg, 40 mg, 45 mg, 50 mg, 55 mg, or 60 mg. In some embodiments, the amount of an API in a drug dosage form is about any of 1 mg, 1.5 mg, 1.75 mg, 2 mg, 2.5 mg, 3 mg, 3.5 mg, 4 mg, 4.5 mg, 5 mg, 6 mg, 7 mg, 8 mg, 9 mg, 10 mg, 11 mg, 12 mg, 13 mg, 14 mg, 15 mg, 20 mg, 25 mg, 30 mg, 35 mg, 40 mg, 45 mg, 50 mg, 55 mg, or 60 mg.

Release Profile

In some embodiments, the drug dosage forms described herein provide specific release profiles of the drugs contained within. In certain embodiments, the drug dosage forms described herein provide immediate release profile. In some embodiments, the drug dosage forms described herein provide sustained release profile. In some embodiments, the drug dosage forms provide a zero-order release profile, a first-order release profile, a delayed release profile, a pulsed release profile, an iterative pulsed release profile, or a combination thereof.

The release profile, e.g., sustained release profile, of a drug dosage form may be evaluated using an in vitro dissolution rate of the drug dosage form. In some embodiments, the desired drug release profile, e.g., sustained release profile, of a drug dosage form is similar, e.g., equivalent or bioequivalent, to the in vitro dissolution rate of the drug dosage form. In some embodiments, the desired drug release profile of a drug dosage form is similar, e.g., equivalent or bioequivalent, to the in vivo drug release profile of the drug dosage form. In some embodiments, the in vivo drug release profile of a drug dosage form is based on evaluation of the in vitro dissolution rate of the drug dosage form. In some embodiments, the desired drug release profile of a drug dosage form is similar, e.g., equivalent or bioequivalent, to the release profile of a reference drug dosage form. Methods for in vitro dissolution testing and determining dissolution similarity are known in the art and the U.S. Food and Drug Administration has provided industry guidance on such methods (see Guidance for Industry; Dissolution Testing of Immediate Release Solid Oral Dosage Forms; CDER; August 1997).

Methods for in vitro dissolution testing include a logarithmic curve method, probability unit method, exponential model method, Weibull method, and Gompertz method. Statistical analysis methods for determining dissolution similarity of two dissolution profiles, e.g., an experimentally determined dissolution profile and a desired drug release profile, comprise regression analysis, ANOVA, similarity factor method, varying factor method, Splitpolt method, and Chow's method. In some embodiments, the dissolution similarity is evaluated using the similarity factor. In some embodiments, the dissolution similarity is evaluated using Chow's method.

In some embodiments, the drug dosage forms described herein provide release of the drugs contained within according to a sustained release profile. In some embodiments, the drug dosage forms described herein provide controlled (e.g., desired) release of the drugs contained within over at least about 4 hours, such as at least about any of 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. In some embodiments, the drug dosage forms described herein provide controlled (e.g., desired) release of the drugs contained within over about any of 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours.

In some embodiments, the sustained release profile comprises a zero-order release profile, a first-order release profile, a delayed release profile, a pulsed release profile, an iterative pulsed release profile, or a combination thereof.

In some embodiments, the drug dosage forms described herein provide release of the drugs contained within according to an immediate release profile.

In some embodiments, the immediate release profile is release of substantially all of the drugs of a drug dosage form within about 60 minutes of administration, such as within about any of 55 minutes, 50 minutes, 45 minutes, 40 minutes, 35 minutes, 30 minutes, 25 minutes, 20 minutes, 15 minutes, 10 minutes, 9 minutes, 8 minutes, 7 minutes, 6 minutes, 5 minutes, 4 minutes, 3 minutes, 2 minutes, or 1 minute of administration.

In some embodiments, the immediate release profile is release of at least about 85% of the drugs of a drug dosage form, such as release of at least about any of 87.5%, 90%, 92.5%, 95%, 97.5%, or 100%, in less than about 15 minutes, such as less than about any of 14 minutes, 13 minutes, 12 minutes, 11 minutes, 10 minutes, 9 minutes, 8 minutes, 7 minutes, 6 minutes, 5 minutes, 4 minutes, 3 minutes, 2 minutes, or 1 minute.

In some embodiments, the immediate release profile is a burst release profile. In some embodiments, the immediate release profile is a bolus release profile.

Drug Dosage Forms with Configurations of Compartmentation

In some embodiments, the drug dosage form described herein comprises a shell defining a first compartment and a second compartment, wherein said shell comprises a first material soluble at a first gastrointestinal site, and a second material soluble at a second gastrointestinal site; a first active pharmaceutical ingredient (API) loaded in the first compartment; and a second active pharmaloaded ingredient loaded in the second compartment.

As used herein, a "shell" refers to a structure that forms an enclosed compartment or cavity that contains an API. A shell can include uniform material or discontinuous parts formed by different materials. A shell can be of any size and shape that are suitable for oral administration.

In some embodiments, the shape of the shell comprises a cylinder, oval, bullet shape, arrow head shape, triangle, arced triangle, square, arced square, rectangle, arced rectangle, diamond, pentagon, hexagon, octagon, half moon, almond, or a combination thereof, wherein the largest dimension crossing the drug dosage form, e.g., largest diameter, is about any of 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm.

In some embodiments, the largest dimension crossing the shell, e.g., largest diameter, is about 1 mm to about 25 mm, such as any of about 2 mm to about 10 mm, about 5 mm to about 12 mm, about 8 mm to about 15 mm, about 5 mm to about 10 mm, or about 7 mm to about 9 mm. In some embodiments, the largest dimension crossing the shell, e.g., largest diameter, is less than about 25 mm, such as less than about any of 24 mm, 23 mm, 22 mm, 21 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, 5 mm, 4 mm, 3 mm, 2 mm, or 1 mm. In some embodiments, the largest dimension crossing the shell, e.g., largest diameter, is greater than about 1 mm, such as greater than about any of 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm. In some embodiments, the largest dimension crossing the shell, e.g., largest diameter, is about any of 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm.

In some embodiments, the shell has a thickness of about 1 mm to about 25 mm, such as any of about 2 mm to about 10 mm, about 5 mm to about 12 mm, about 8 mm to about 15 mm, about 5 mm to about 10 mm, or about 7 mm to about 9 mm. In some embodiments, the shell has a thickness of less than about 25 mm, such as less than about any of 24 mm, 23 mm, 22 mm, 21 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, 5 mm, 4 mm, 3 mm, 2 mm, or 1 mm. In some embodiments, the shell has a thickness of greater than about 1 mm, such as greater than about any of 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm. In some embodiments, the shell has a thickness of about any of 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm.

In certain embodiments, the shell is an oval tablet having a dimension of around a mm×b mm, wherein a is 5 to 15 and b is 2 to 10. In certain embodiments, the shell has a capsule shape.

As used herein, a "compartment" refers to a chamber or an enclosed cavity formed within the drug dosage form. In some embodiment, a compartment is filled or loaded with an API or a material different from that from the compartment. In some embodiment, a compartment has empty space contained within.

In some embodiment, the shape of the compartment comprises a cylinder, oval, bullet shape, arrow head shape, triangle, arced triangle, square, arced square, rectangle, arced rectangle, diamond, pentagon, hexagon, octagon, half moon, almond, or a combination thereof, wherein the largest dimension crossing the chamber, e.g., largest diameter, is about any of 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm.

In some embodiments, the compartment has a volume of about any of 0.5 mm$^3$, 0.6 mm$^3$, 0.7 mm$^3$, 0.8 mm$^3$, 0.9 mm$^3$, 1 mm$^3$, 1.1 mm$^3$, 1.2 mm$^3$, 1.3 mm$^3$, 1.4 mm$^3$, 1.5 mm$^3$, 1.6 mm$^3$, 1.7 mm$^3$, 1.8 mm$^3$, 1.9 mm$^3$, 2 mm$^3$, 3 mm$^3$, 4 mm$^3$, 5 mm$^3$, 6 mm$^3$, 7 mm, 8 mm$^3$, 9 mm$^3$, 10 mm$^3$, 15 mm$^3$, 20 mm$^3$, 25 mm$^3$, 30 mm$^3$, 35 mm$^3$, 40 mm$^3$, 45 mm$^3$, 50 mm$^3$, 55 mm$^3$, 60 mm$^3$, 65 mm$^3$, 70 mm$^3$, 75 mm$^3$, 80 mm$^3$, 85 mm$^3$, 90 mm$^3$, 95 mm$^3$, 100 mm$^3$, 125 mm$^3$, 150 mm$^3$, 175 mm$^3$, or 200 mm$^3$.

In some embodiments, the compartment is enclosed by a series of walls. In some embodiments, the walls are part of the shell. In some embodiments, the walls are formed by an API or a material other than that forms the shell. In some embodiments, the walls have a thickness of about any of 0.05 mm, 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.85 mm, 0.9 mm, 0.95 mm, 1 mm, 1.1 mm, 1.2 mm, 1.3 mm, 1.4 mm, 1.5 mm, 1.6 mm, 1.7 mm, 1.8 mm, 1.9 mm or 2 mm.

Drug Dosage Forms with Coatings

In some embodiments, the drug dosage form described herein comprises a first particle, wherein the first particle comprises a first API wrapped by a first coat, wherein the first coat has a first thickness and dissolves at a first gastrointestinal site to release the first API; a second particle, wherein the second particle comprises a second API wrapped by a second coat, wherein the second coat has a second thickness and dissolves at a second gastrointestinal site to release the second API; a third particle, wherein the third particle comprises a third API wrapped by a third coat, wherein the third coat has a third thickness and dissolves at a third gastrointestinal site to release the third API; and a shell defining a compartment, wherein the first, the second and the third particles locate in the compartment.

In some embodiments, the particles have a diatermer of about any of 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm.

In some embodiments, the coats are formed by a material selected from the group consisting of polyvinylpyrrolidone (povidone), polyvinylpyrrolidone-polyvinyl acetate copolymer (copovidone), crospovidone, mixtures of polyvinyl acetate and povidone, methacrylic acid copolymers, aminomethyl acrylic acid copolymer, methacrylic acid ester copolymer, ethyl acrylate, a copolymer of an anionic polymer and methacrylic acid, a copolymer of a cationic polymer and dimethylaminoethyl methacrylate, a butyl acrylate, a copolymer of methacrylic acid and methyl acrylate, ethyl methacrylate copolymer, butyl methacrylate copolymer, an ethyl acrylate monomethacrylate copolymer, an ethyl acrylate monomethacrylate copolymer, a copolymer of methyl methacrylate and trimethylaminoethyl methacrylate, ethyl acrylate/methyl methacrylate/trimethylaminoethyl methacrylate polymers, methyl cellulose, ethyl Cellulose, polyvinyl acetate phthalate, hypromellose succinate, polyethylene glycol-polyvinyl alcohol copolymer, hydroxypropyl methylcellulose phthalate or hypromellose phthalate, polyethylene glycol 15-hydroxystearate, methyl methacrylate and diethylaminoethyl methacrylate copolymer, polymethyl acrylate-polymethylmethacrylate-polymethacrylate copolymer, polymethyl methacrylate, N-dimethylaminoethyl methacrylate, polyvinylcaprolactam-polyvinyl acetate-polyethylene glycol graft copolymer, polybutylmethacrylate-poly N,N-dimethyl aminoethylmethacrylate-polymethylmethacrylate copolymer, polyvinyl alcohol, hydroxypropylcellulose, polyethylene oxide, polyoxyethylene, polyoxyethylene hydrogenated castor oil, a copolymer of propylene oxide and ethylene oxide (poloxamer), polyethylene glycol, polyethylene glycol cetostearyl ether, hyperbranched polyesteramide, hydroxypropyl Methyl cellulose or hypromellose, hydroxyethyl cellulose, cellulose acetate, polysorbate (Tween), carbomer, lactose, microcrystalline cellulose, pregelatinized starch, vitamin E polyethylene glycol alcohol succinate, polydimethylsiloxane, xanthan gum, polylactic acid, polylactide-polylactic acid copolymer, polycaprolactone, carnauba wax, glyceryl palmitostearate, hydrogenated castor oil, Cellulose acetate butyrate, polyvinyl acetate, polyethylacrylate-polymethylmethacrylate-polytrimethyl ammonium chloride ethylmethacrylate copolymer, polyethylene-polyvinyl acetate copolymer and shell poly Sugar, beeswax, polyethylene glycol methacrylate, and combinations thereof.

In some embodiments, the coat has a thickness of about any of 0.05 mm, 0.06 mm, 0.07 mm, 0.08 mm, 0.09 mm, 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.85 mm, 0.9 mm, 0.95 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm or 10 mm.

Drug Dosage Forms with Multi-Layered Structure

In some embodiments, the drug dosage form comprises a cylindrical shell defining a cavity, the cylindrical shell having an upper end and a bottom end, wherein the cylindrical shell is formed by an insoluble material, and wherein the upper and the bottom ends are covered by a first material soluble in a first gastrointestinal site; and a first and a second APIs, both loaded in the cavity, wherein the first and the second APIs are separated by a second material soluble in a second gastrointestinal site, wherein the first material, the first API, the second material and the second material are configured as a multi-layered structure. In some embodiments, the first material is a stomach soluble material, and the second material is a large intestine soluble material. In some embodiments, the first material is a large intestine soluble material. In some embodiments, first material is a colon soluble material.

In some embodiment, each layer of the multi-layered structure has a thickness of about any of 0.05 mm, 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.85 mm, 0.9 mm, 0.95 mm, or 1 mm.

Manufacture of the Dosage Form

The controlled release dosage forms disclosed herein can be manufactured using any appropriate process. In certain embodiments, the dosage forms are produced using three-dimensional printing (3D printing).

As used herein, 3D printing refers to a process that produce 3D objects layer-by-layer from digital designs. The basic process of 3D printing has been described in U.S. Pat. Nos. 5,204,055; 5,260,009; 5,340,656; 5,387,380; 5,503,785; and 5,633,021. Additional U.S. patents and applications related to 3D printing include: U.S. Pat. Nos. 5,490,962; 5,518,690; 5,869,170; 6,530,958; 6,280,771; 6,514,518; 6,471,992; 8,828,411; U.S. PG Pub. Nos: 2002/0015728; 002/0106412; 2003/0143268; 2003/0198677; 2004/0005360. Reference can be made to the patents and applications listed above for a detailed description of 3D printing.

Different 3D printing methods have been developed for dosage form manufacturing in terms of raw materials, equipment and solidification. These 3D printing methods include binder deposition (see L Gibson et al. (2015) Additive Manufacturing Technologies: 3D Printing, Rapid Prototyping, and Direct Digital Manufacturing. 2 ed. Springer, New York; W. E. Katstra et al. (2000) Oral dosage forms fabricated by three dimensional printing, J. Control Release 66: 1-9; W. E. Katstra et al. (2001) Fabrication of complex oral delivery forms by three dimensional printing, Dissertation in Materials Science and Engineering, Massachusetts Institute of Technology; H. Lipson et al. (2013) Fabricated: The New World of 3D printing, John Wiley & Sons, Inc.; G. Jonathan, A. Karim (2016) 3D printing in pharmaceutics: a new tool for designing customized drug delivery systems, Int. J. Pharm. 499: 376-394), material jetting (see G. Jonathan, A. Karim (2016) 3D printing in pharmaceutics: a new tool for designing customized drug delivery systems, Int. J. Pharm. 499: 376-394), extrusion (see L Gibson et al. (2015) Additive Manufacturing Technologies: 3D Printing, Rapid Prototyping, and Direct Digital Manufacturing. 2 ed. Springer, New York) and photopolymerization (see F. P. Melchels et al. (2010) A review on stereolithography and its application in biomedical engineering. Biomaterials 31: 6121-30).

In certain embodiments, the dosage forms disclosed herein are manufactured using binder deposition methods. In a typical binder deposition, inkjet printers spray binder-containing liquid formulation in small droplets at precise speeds, motions and sizes onto a powder bed, which contains a layer of powders. Unbound powder severs as the support material for free-standing or porous structures. A new layer of power is then added atop, followed by the next round of binder spray. The liquid formulations inside the printer may contain a binder only, and the powder bed may contain the active ingredient with additional excipients. Alternatively, APIs can be jetted onto powder beds as solutions or nanoparticulate suspensions.

In certain embodiments, the dosage forms disclosed herein are manufactured using extrusion methods. In an extrusion process, material is extruded from robotically-actuated nozzles. Unlike binder deposition, which requires a powder bed, extrusion methods can print on any substrate. A variety of materials can be extruded for 3D printing, including thermoplastic materials disclosed herein, pastes and colloidal suspensions, silicones and other semisolids. Typically, the thermoplastic material is melted in the 3D printer before being extruded to form the substrate. In certain embodiment, appropriate extruders include without limitation, single or twin screw extruders with the temperature within the extruder at a range from 50° C. to 180° C. and from 80° to 140° C. In general, the extrusion process can be conducted at temperatures 10° to 40° C. above the glass transition (Tg) of the thermoplastic material. Once at a suitable temperature for use in the three-dimensional printer, the thermoplastic material can be deposited to the three-dimensional printing surface. The shape and size of the substrate and the compartment fabricated by the thermoplastic material can be controlled by programing the three-dimensional printing process. (see L Gibson et al. (2015) Additive Manufacturing Technologies: 3D Printing, Rapid Prototyping, and Direct Digital Manufacturing. 2 ed. Springer, New York).

The manufacturing instructions for a print job may be generated a variety of ways, including direct coding, derivation from a solid CAD model, or other means specific to the 3D printing machine's computer interface and application software. These instructions may include information on the number and spatial placement of droplets, and on general print parameters such as the drop spacing in each linear dimension (X, Y, Z), and volume or mass of fluid per droplet. For a given set of materials, these parameters may be adjusted in order to refine the quality of structure created. The overall resolution of the structure created is a function of the powder particle size, the fluid droplet size, the print parameters, and the material properties.

In certain embodiments, the drug content is fabricated in the same process of the matrix. In certain embodiments, the drug content is fabricated before the making of the matrix and loaded into the compartment during or after the matrix is fabricated.

Because of its ability of handling a range of pharmaceutical materials and control both composition and architecture locally, 3D printing is well suited to the fabrication of dosage forms with complex geometry and composition in accordance with the present invention.

The drug dosage forms disclosed in the present application can be printed on a commercial scale. For example, in some embodiments, the methods disclosed herein may be used to 3D print about 10,000 to about 100,000 tablets of a drug dosage form per hour. In some embodiments, each drug dosage form of a commercial batch possesses or substantially complies with one or more pre-determined dosage form characteristics described herein, e.g., printing uniformity, precision of layer thickness(es), precision of layer surface area, precision of layer active agent(s) mass fraction, precision of dosage form shape, size, and weight, precision of active agent(s) amount, and precision of active agent release profile. In some embodiments, at least about 80%, such as at least about any of 85%, 90%, or 95%, of drug dosage forms of a commercial batch possess or substantially comply with one or more pre-determined dosage form characteristics described herein, e.g., printing uniformity, precision of layer thickness(es), precision of layer surface area, precision of layer active agent(s) mass fraction, precision of dosage form shape, size, and weight, precision of active agent(s) amount, and precision of active agent release profile.

EXEMPLARY EMBODIMENTS

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, the embodiments described herein can be practiced without these specific details. In other instances, methods, procedures and components have not been described in detail so as not to obscure the related relevant function being described. Also, the description is not to be considered as limiting the scope of the implementations described herein. It will be understood that descriptions and characterizations of the embodiments set forth in this disclosure are not to be considered as mutually exclusive, unless otherwise noted.

Embodiment 1

FIG. 1 shows an exemplary drug dosage form released at a particular site of the gastrointestinal tract. Referring to FIG. 1, a drug dosage form 100 includes a shell 101, a first API 112, a second API 122 and a third API 132. The shell 101 includes a stomach soluble material 111, a small intestine soluble material 121, and a colon soluble material 131. The stomach soluble material 111 forms a first compartment 110, the small intestine soluble material 121 forms a second compartment 120, and the colon soluble material 131 forms a third compartment 130. The first API 112 is located in the first compartment 110, the second API 122 is located in the second compartment 120, and the third API 132 is located in the third compartment 130. The small intestine soluble material 121 is located in a fourth compartment 140 formed by the stomach soluble material 111 and the colon soluble material 131 is located in the fifth compartment 150 formed by the stomach soluble material 111.

After a patient orally administers the drug dosage form 100, the stomach soluble material 111 dissolves in the gastric fluid environment, releasing the first API 112 while exposing the small intestine soluble material 121 and the colon soluble material 131 to the gastric fluid environment. The small intestine soluble material 121 and the colon soluble material 131 are not soluble in the gastric fluid. The the small intestine soluble material 121 dissolves upon entering the small intestine, releasing the second API 122. The colon soluble material 131 remains insoluble in the small intestine and dissolves and releases the third API 132 in the colon. According to the present embodiment, it is possible to achieve specific drug release in the stomach, small intestine and colon, respectively.

Embodiment 2

Figure 2:
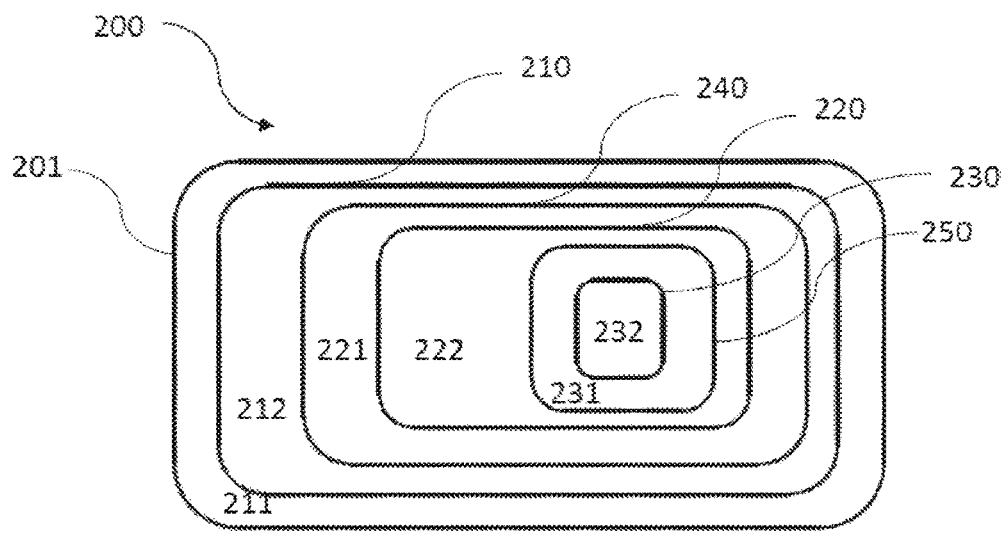
FIG. 2 shows an exemplary drug dosage form of controlled release at specific gastrointestinal site.

FIG. 2 shows an exemplary drug dosage form released at a particular site of the gastrointestinal tract. Referring to FIG. 2, a drug dosage form 200 includes a shell 201, a first API 212, a second API 222 and a third API 232. The shell 201 includes a stomach soluble material 211, a small intestine soluble material 221, and a colon soluble material 231. The stomach soluble material 211 forms a first compartment 210, the small intestine soluble material 221 forms a second compartment 220, and the colon soluble material 231 forms a third compartment 230. The first API 212 is located in the first compartment 210, the second API 222 is located in the second compartment 220, and the third API 232 is located in the third compartment 230. The small intestine soluble material 221 is located in a fourth compartment 240 formed by the first API 212, and the colon soluble material 231 is located in the fifth compartment 250 formed by the second API 222.

After a patient orally administers the drug dosage form 200, the stomach soluble material 211 dissolves in the gastric fluid environment, releasing the first API 212 while exposing the small intestine soluble material 221. The small intestine soluble material 221 is not soluble in the gastric fluid. The small intestine soluble material 221 dissolves upon entering the small intestine, releasing the second API 222 and exposing the colon soluble material 231 to the small intestine environment. The colon soluble material 231 remains insoluble in the small intestine and dissolves and releases the third API 232 in the colon. According to the present embodiment, it is possible to achieve specific drug release in the stomach, small intestine and colon, respectively.

Embodiment 3

Figure 3A:
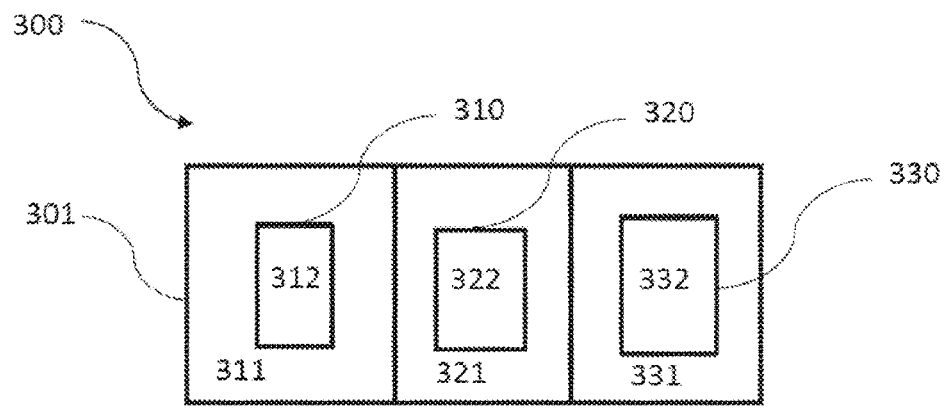
FIG. 3A shows an exemplary drug dosage form of controlled release at specific gastrointestinal site.
Figure 3B:
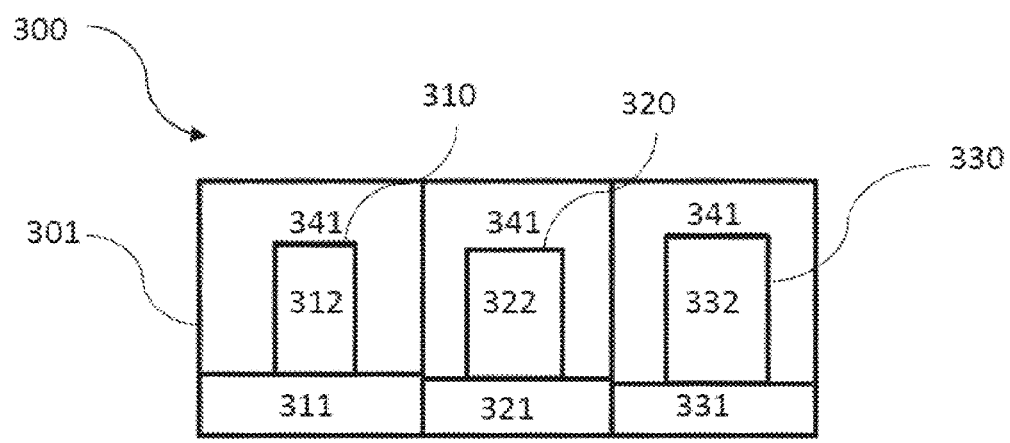
FIG. 3B shows an exemplary drug dosage form of controlled release at specific gastrointestinal site.

FIGS. 3A and 3B show respectively an exemplary drug dosage form released at a particular site of the gastrointestinal tract. Referring to FIG. 3A, in one embodiment, a drug dosage form 300 includes a shell 301, a first API 312, a second API 322 and a third API 332. The shell 301 includes a stomach soluble material 311, a small intestine soluble material 321, and a colon soluble material 331. The stomach soluble material 311 forms a first compartment 310, the small intestine soluble material 321 forms a second compartment 320, and the colon soluble material 331 forms a third compartment 330. The first API 312 is located in the first compartment 310, the second API 322 is located in the second compartment 320, and the third API 332 is located in the third compartment 330. The stomach soluble material 311, small intestine soluble material 321 and the colon soluble material 331 is juxtaposed.

Referring to FIG. 3B, in another embodiment, a drug dosage form 300 includes a shell 301, a first API 312, a second API 322 and a third API 332. The shell 301 includes a stomach soluble material 311, a small intestine soluble material 321, a colon soluble material 331, and an insoluble material 341. The stomach soluble material 311 and the insoluble material 341 together form a first compartment 310, the small intestine soluble material 321 and the insoluble material 341 together form a second compartment 320, and the colon soluble material 231 and the insoluble material 341 together form a third compartment 330. Each of the first compartment 310, the second compartment 320 and the third compartment 330 has an opening that is covered by the stomach soluble material 311, the small intestine soluble material 321, and the colon soluble material 331, respectively. The insoluble material 341 forms the rest part of the compartments except the openings. The first API 312 is located in the first compartment 310, the second API 322 is located in the second compartment 320, and the third API 332 is located in the third compartment 330.

After a patient orally administers the drug dosage form 300, the stomach soluble material 311 dissolves in the gastric fluid environment, releasing the first API 312. The small intestine soluble material 321 is not soluble in the gastric fluid. The small intestine soluble material 321 dissolves upon entering the small intestine, releasing the second API 322. The colon soluble material 331 remains insoluble in the stomach and the small intestine and dissolves and releases the third API 332 in the colon. According to the present embodiment, it is possible to achieve specific drug release in the stomach, small intestine and colon, respectively.

Embodiment 4

Figure 4:
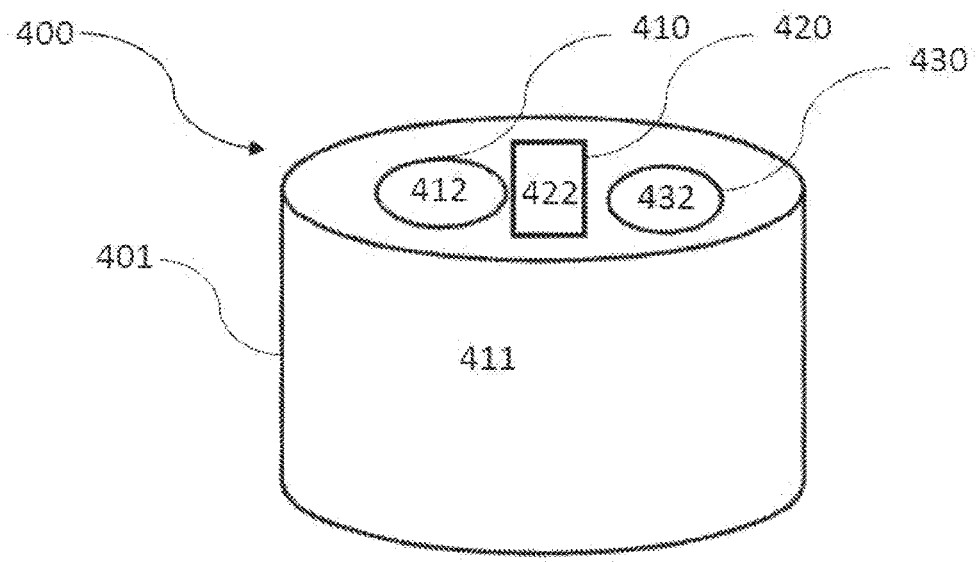
FIG. 4 shows an exemplary drug dosage form of controlled release at specific gastrointestinal site.

FIG. 4 shows an exemplary drug dosage form released at a particular site of the gastrointestinal tract. Referring to FIG. 4, a drug dosage form 400 includes a shell 401, a first API 412, a second API 422 and a third API 432. The shell 401 includes a material 411 dissolvable at a specific site of the gastrointestinal tract. The gastrointestinal specific site-dissolved material 411 forms a first compartment 410, a second compartment 420, and a third compartment 430. The first API 412 is located in the first compartment 410, the second API 422 is located in the second compartment 420, and the third API 432 is located in the third compartment 430. The first compartment 410, the second compartment 420, and the third compartment 430 may take different configurations such as a pie shape, a cone shape, a pyramid shape, a cylinder shape, a cube shape, a cuboid shape, a triangle or a polygon shape, a tetrahedron shape or a combination of these shapes.

After a patient orally administers the drug dosage form 400, the gastrointestinal specific site-dissolved material 411 dissolves in a specific site of the gastrointestinal tract (e.g., in gastric fluid), releasing the first API 412, the second API 422 and the third API 432.

Embodiment 5

Figure 5:
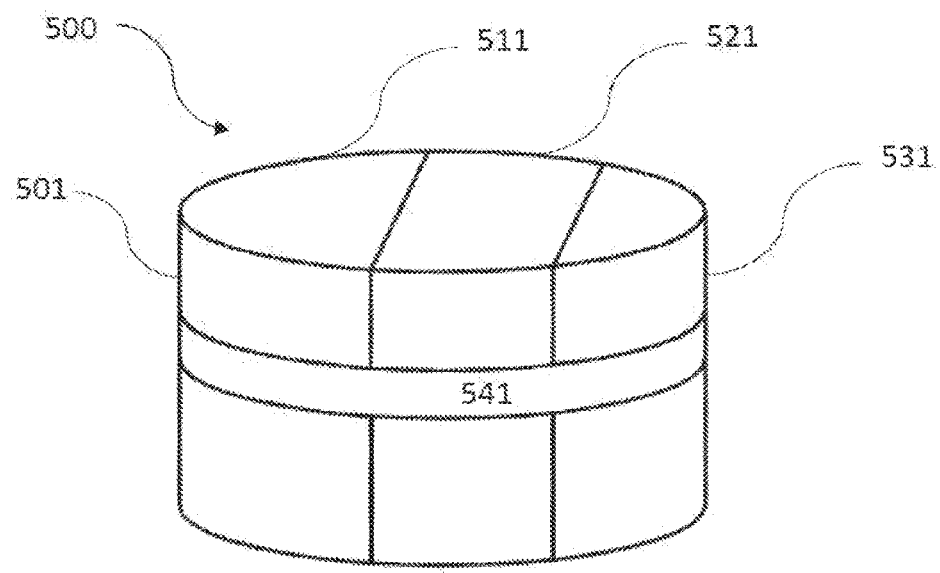
FIG. 5 shows an exemplary drug dosage form of controlled release at specific gastrointestinal site.

FIG. 5 shows an exemplary drug dosage form released at a particular site of the gastrointestinal tract. Referring to FIG. 5, the drug dosage form 500 includes a shell 501. The shell 501 includes a stomach soluble material 511, a small intestine soluble material 521, a colon soluble material 531, and an insoluble material 541. The structures of the stomach soluble material 511, the small intestine soluble material 521, and the colon soluble material 531 are basically similar to those of Embodiment 3. The difference is that the drug dosage form in this embodiment further includes a barrier formed by the insoluble material 541 to separate the drug dosage form into upper and lower layers.

After the patient orally administers the dosage form 500, the stomach soluble material dissolves in the gastric fluid environment, releasing the first API. The small intestine soluble material 521 is insoluble in the gastric fluid environment. The small intestine soluble material 521 dissolves after entering the small intestine, releasing the second API. The colon soluble material 531 is not soluble in either gastric and intestinal conditions and dissolves and releases the third API in the large intestine. According to the present embodiment, it is possible to achieve the release of a specific drug in the stomach, small intestine and large intestine, respectively.

Embodiment 6

Figure 6:
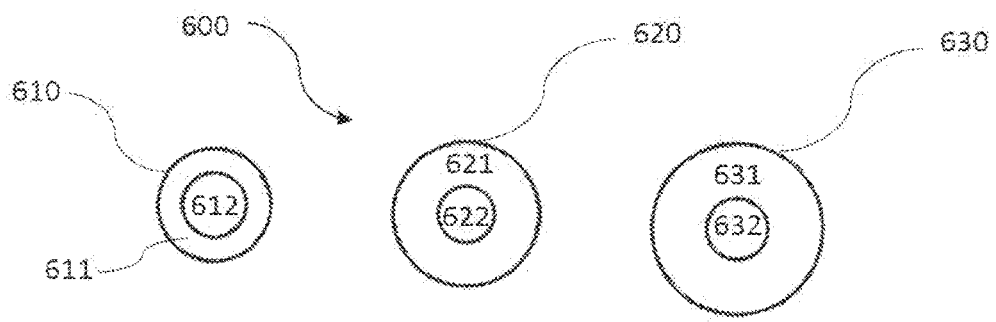
FIG. 6 shows an exemplary drug dosage form of controlled release at specific gastrointestinal site.

FIG. 6 shows an example of a drug dosage form that is released at a particular site of the gastrointestinal tract. Referring to FIG. 6, the drug dosage form 600 contains a first drug particle 610, a second drug particle 620, and a third drug particle 630 in a shell (e.g., a capsule) forming a sealed compartment. The first drug particle 610 include a first API 612 that is coated by a first coat 611; the second drug particles 620 include a second API 622 that is coated by a second coat 621; the third drug particle 630 includes a third API 632 coated by a third coat 631. The first coat 611, the second coat 621, and the third coat 631 may be formed by different materials that dissolve in specific parts of the gastrointestinal tract and/or have different thicknesses.

After a patient orally administrates the dosage form 600, the first coat 611, the second coat 621 and the third coat 631 can be released in a specific part of the gastrointestinal tract due to different materials and/or thicknesses. For example, thin coat dissolves first, allowing the coated drug to be released in the stomach. A thicker coat, on the other hand, erodes later to allow the coated drug to travel to the intestine for release.

Embodiment 7

Figure 7:
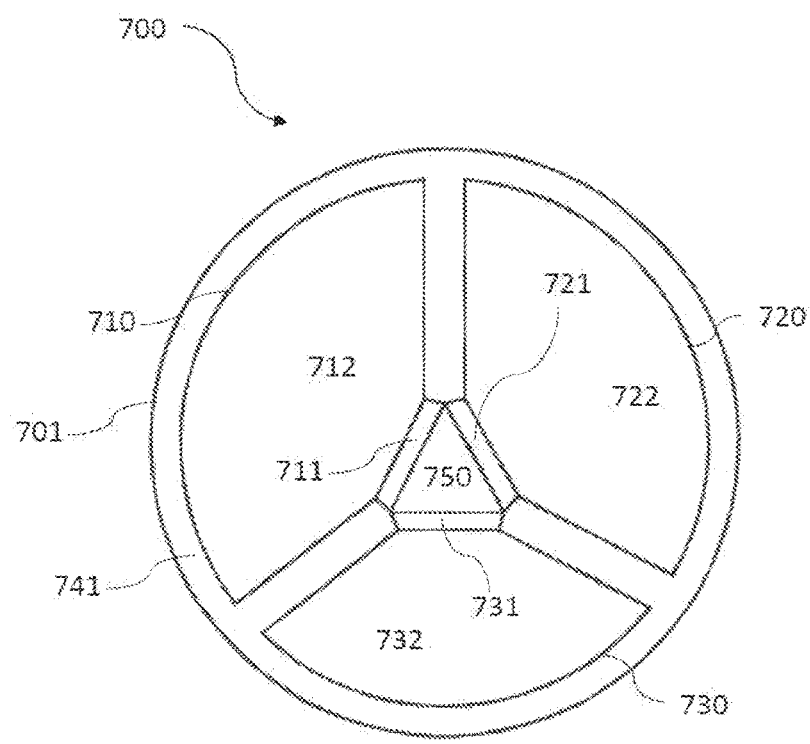
FIG. 7 shows an exemplary drug dosage form of controlled release at specific gastrointestinal site.

FIG. 7 shows an exemplary drug dosage form released at a particular site of the gastrointestinal tract. Referring to FIG. 7, a drug dosage form 700 includes a shell 701, a first API 712, a second API 722 and a third API 732. The shell 701 has a tablet structure with a cavity 750 in the center. The shell 701 includes a stomach soluble material 711, a small intestine soluble material 721, a colon soluble material 731, and an insoluble material 741. The stomach soluble material 711 and the insoluble material 741 together form a first compartment 710. The small intestine soluble material 721 and the insoluble material 741 together form a second compartment 720. The colon soluble material 731 and the insoluble material 741 together form a third compartment 730. The first compartment 710, the second compartment 720 and the third compartment 730 are pie-shaped. The stomach soluble material 711, the small intestinal soluble material 721 and the colon soluble material 731 respectively form an opening of the pie-shaped compartment, and the other part of the pie-shaped compartment is formed by the insoluble material 741.

After a patient orally administrates the dosage form 700, the stomach soluble material 711 contacts and dissolves in the gastric fluid environment through the cavity 750 to release the first API 712. The pie-shaped configuration of the first compartment 710 causes the first API 712 to be released at a zero-order rate. The small intestine soluble material 721 and the colon soluble material 731 do not dissolve in the gastric fluid environment. After the drug dosage form 700 enters the small intestine, the small intestine soluble material 721 contacts and dissolves in the small intestinal environment through the cavity 750, releasing the second API 722. The pie-shaped configuration of the second compartment 720 causes the second API 722 to be released at a zero-order rate. Colon soluble material 731 does not dissolve in the small intestinal environment. After the drug dosage form 700 enters the colon, the colon soluble material 731 contacts and dissolves in the colon environment through the cavity 750, releasing the third API 732. The pie-shaped configuration of the third compartment 730 causes the third API 732 to be released at a zero-order rate. According to the present embodiment, it is possible to achieve release of a specific drug at a zero-order rate in the stomach, small intestine and colon, respectively.

Embodiment 8

Figure 8:
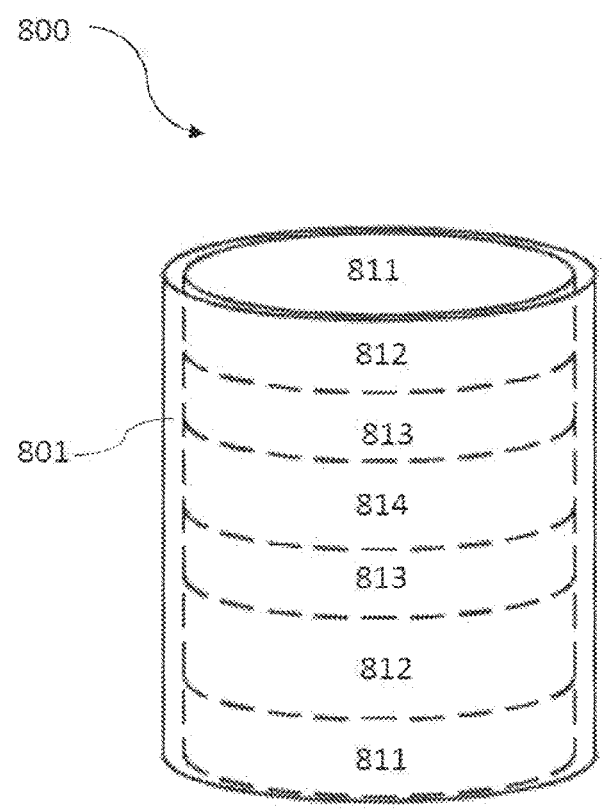
FIG. 8 shows an exemplary drug dosage form of controlled release at specific gastrointestinal site.

FIG. 8 shows an exemplary pharmaceutical dosage form that is released at a particular site of the gastrointestinal tract. Referring to FIG. 8, the drug dosage form 800 has a cylindrical configuration. The side of the cylinder is surrounded by a shell 801 formed of an insoluble material. The upper and lower end surfaces of the cylinder are covered by a layered structure formed by a stomach soluble material 811. From the outside of the upper and lower end surfaces to the inside, the drug dosage form has layered structures formed by the stomach soluble material 811, by the first API 812, by the colon soluble material 813, and by the second API 814.

After a patient orally administers the dosage form 800, the stomach soluble material 811 dissolves in the gastric fluid environment and releases the first API 812 at a zero-order rate. Colon soluble material 813 does not dissolve in the gastric fluid environment. The colon soluble material 813 dissolves in the colon environment after the drug dosage form 800 enters the colon, releasing the second API 814 at a zero-order rate. According to the present embodiment, it is possible to achieve release of a specific drug at the zero-order rate in the stomach and the colon, respectively.

Embodiment 9

Figure 9:
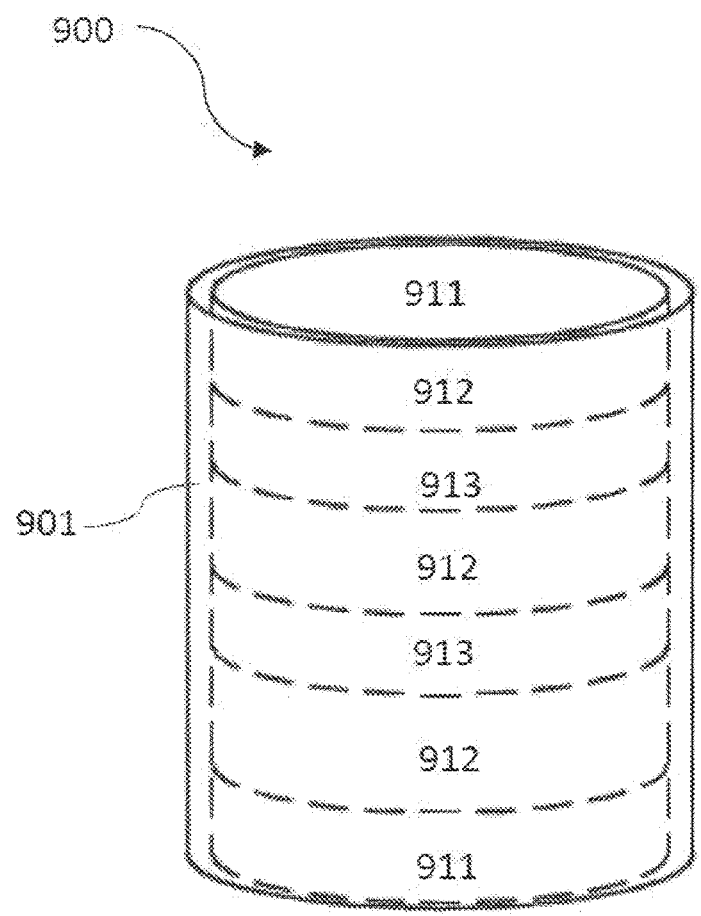
FIG. 9 shows an exemplary drug dosage form of controlled release at specific gastrointestinal site.

FIG. 9 shows an exemplary pharmaceutical dosage form released at a particular site of the gastrointestinal tract. Referring to FIG. 9, a drug dosage form 900 has a cylindrical configuration. The side of the cylinder is covered by a shell 901 formed of an insoluble material. The upper and lower end surfaces of the cylinder are covered by a layered structure formed by a colon soluble material 911. From the outside of the upper and lower end surfaces, the dosage form has layered structures formed by the colon soluble material 911, by the first API 912, by the colon soluble (or stomach soluble or small intestine soluble) material 913, and by the first API 912.

After a patient has taken the drug dosage form 900, the colon soluble material 911 does not dissolve in the gastric fluid environment and in the small intestine. After the drug dosage form 900 enters the colon, the colon soluble material 911 dissolves in the colon environment, releasing the second API 912 at zero-order rate. The colon soluble (or stomach soluble or small intestine soluble) material 913 dissolves in the colon environment and continues to release the second API 912 at a zero-order rate. According to the present embodiment, it is possible to achieve release of a specific drug at a zero-order rate in the colon.

EXAMPLE 1

This example illustrates a drug dosage form as shown in FIG. 3A. Referring to FIG. 3A, a drug dosage form 300 includes a shell 301, a first API 312, a second API 322 and a third API 332. The shell 301 includes a stomach soluble material 311, a small intestine soluble material 321, and a colon soluble material 331. The stomach soluble material 311 forms a first compartment 310, the small intestine soluble material 321 forms a second compartment 320, and the colon soluble material 331 forms a third compartment 330. The first API 312 is located in the first compartment 310, the second API 322 is located in the second compartment 320, and the third API 332 is located in the third compartment 330. The stomach soluble material 311, small intestine soluble material 321 and the colon soluble material 331 is juxtaposedly linked.

The design of the drug dosage form was as follows: the stomach soluble material 311 was consisted of KOLLIDON® VA64 (copovidone or vinylpyrrolidone-vinyl acetate copolymer) (80%) and Triethyl Citrate (TEC) (20%); the small intestine soluble material 321 was consisted of 10% of EUDRAGIT® L100 (poly(methacrylic acid, methyl methacrylate) 1:1), 70% of KOLLIDON® VA64 (copovidone or vinylpyrrolidone-vinyl acetate copolymer) and 20% of TEC. The colon soluble material 331 was consisted of EUDRAGIT® S100 (poly(methacrylic acid, methyl methacrylate) 1:2) (10%), KOLLIDON® VA64 (copovidone or vinylpyrrolidone-vinyl acetate copolymer) (65%) and TEC (25%). The stomach soluble material 311 formed a compartment having a wall of thickness of 0.6 mm, the small intestine soluble material 321 and the colon soluble material 331 formed a cell having a wall of thickness of 0.4 mm, respectively. The compartments were filled with drug ingredient of 15% of phenol red, 30% of TEC, and 55% of KOLLIDON® VA64 (copovidone or vinylpyrrolidone-vinyl acetate copolymer).

Preparation of drug dosage form: the dosage form 300 was prepared by fused deposition modeling. According to the shape and size of the drug dosage form, 3D modeling was carried out in the computer by using computer-aided design software. The computer transmits the 3D modeling data to a 3D printer, which used software (repetier-host, version 1.0.0.0) to perform layered slice processing. The corresponding code formed controlled the print head position and trajectory. The pre-mixed raw materials to be printed were added to the feed hopper of the 3D printer. The raw materials were heated to the molten state by the screw, and were extruded from the nozzle. The melt-extruded materials were printed layer by layer on the printing platform along with the print head along X, Y axis movement. The molten material cooled and accumulated layer by layer and adhered to each other, forming the drug dosage form.

Detection the release of drug ingredients: The drug dosage form 300 was added to 900 ml of pH 1.2 hydrochloric acid solution at 50 rpm and the UV absorbance of the hydrochloric acid solution was determined ($\lambda$=505 nm). After 120 minutes, the dosage form was removed and added to pH 6.6 phosphate buffer at a UV absorption wavelength $\lambda$, of 430 nm. After 300 minutes, the dosage form was taken out and added to a pH 7.4 phosphate buffer and the UV absorbance of this buffer was measured ($\lambda$=430 nm). Control samples at a concentration of 0.0236 mg/ml were prepared, measured by UV, absorbance was measured and the solubility at each pH was calculated according to the following formula.

$$\text{Solubility} = \frac{C_{control} \times A_{sample}}{C_{sample} \times A_{control}} \times 100\%$$

Figure 10:
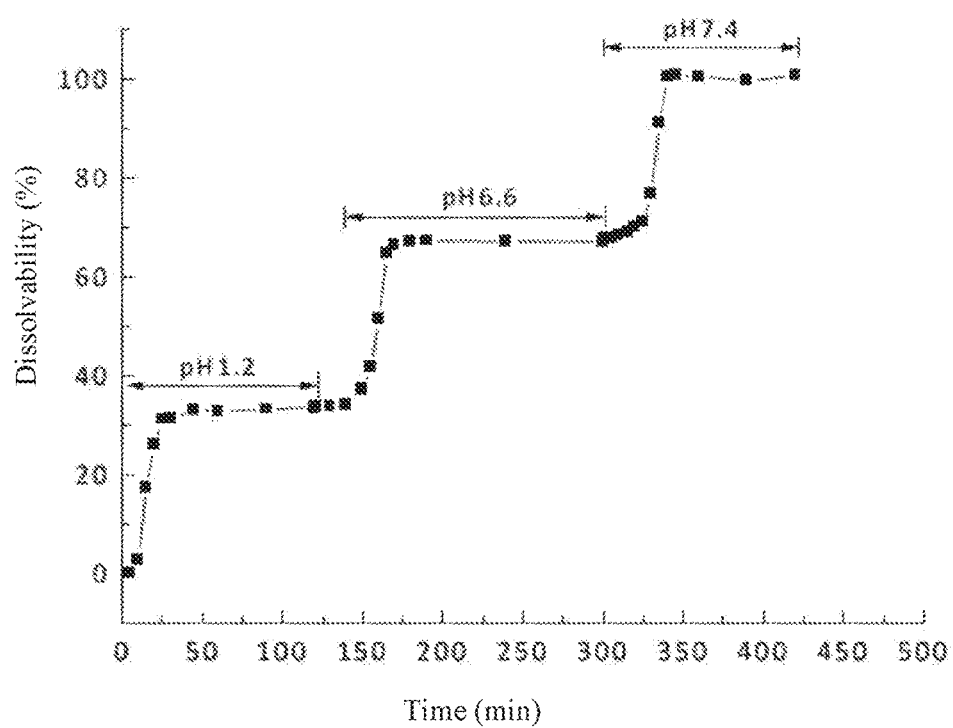
FIG. 10 shows the releasing profile of the drug dosage form of FIG. 3 in HCl solution of pH 1.2, in phosphate solution of pH 6.6 and phosphate solution of pH 7.4.

C control: control sample concentration (mg/ml)
A sample: sample absorbance
C sample: sample concentration (mg/ml)
A control: control sample absorbance The results of the release assay are shown in FIG. 10. After the dosage form was added to the hydrochloric acid solution for 10 minutes, the compartment formed by the stomach soluble material 311 was opened and the drug ingredients in the compartment were released. After 120 minutes in the hydrochloric acid solution, the dosage form was transferred to pH 6.6 buffer. After 30 minutes, the compartment formed by the small intestine soluble material 321 was opened and the drug ingredients inn the compartment were released. After 180 minutes in pH 6.6 buffer, the dosage form was transferred to pH 7.4 buffer. After 30 minutes, the compartment formed by the colon soluble material 331 was opened and the drug ingredients in the compartment were released. The release profile of the drug dosage form can thus be controlled by the shell forming the compartments.

What is claimed is:

1. A cylindrical drug dosage form having an upper end and a bottom end, wherein the cylindrical drug dosage form consists of:
   a cylindrical shell covering the side of the cylindrical drug dosage form but not the upper end and the bottom end, wherein the cylindrical shell consists of an insoluble material selected from the group consisting of poly (ethyl acrylate-methyl methacrylate-trimethyl aminoethyl methacrylate chloride) (poly (EA-MMA-TAMCl)) 1:2:0.2 (molar ratio), poly (EA-MMA-TAMCI) 1:2:0.1 (molar ratio), polyvinyl acetate and povidone mixtures, methacrylic acid ester copolymer, butyl acrylate, methacrylic acid-methylmethacrylate copolymer, ethyl methacrylate-co-methacrylic acid copolymer, butyl acrylate-monobutyl acrylate copolymer, ethyl acrylate-monomethacrylate copolymer, ethyl acrylate-methyl methacrylate copolymer, ethyl acrylate-methyl methacrylate-trimethylaminoethyl methacrylate copolymer, methyl cellulose, ethyl cellulose, hypromellose succinate, hydroxypropyl methylcellulose phthalate, cellulose acetate, polylactic acid, polycaprolactone, carnauba wax, cellulose acetate butyrate, and a combination thereof, wherein the insoluble material does not dissolve in the gastrointestinal tract;
   a first layer and a second layer each consisting of a first material soluble in stomach, wherein the first material is selected from the group consisting of a copolymer of polyvinylpyrrolidone and polyvinyl acetate, polyvinyl alcohol, polyethylene glycol 15-hydroxystearate, polyvinylcaprolactam-polyvinyl acetate-polyethylene glycol graft copolymer, hydroxypropylcellulose, polyethylene oxide, polyethylene glycol, polyethylene glycol cetostearyl ether, hydroxypropylmethylcellulose, hydroxyethylcellulose, carbomer, lactose, vitamin E polyethylene glycol succinate, xanthan gum, and a combination thereof;
   a third and a fourth layer each comprising a first active pharmaceutical ingredient (API);
   a fifth and a sixth layer each consisting of a second material soluble in large intestine, wherein the second material is selected from the group consisting of poly (methacrylic acid-methyl methacrylate) (poly (MA-MMA)) 1:2 (molar ratio), methacrylate copolymer, methacrylic acid-ethyl acrylate copolymer, hydroxypropyl methyl cellulose succinate, and a combination thereof; and
   a seventh layer comprising a second API,
   wherein the cylindrical drug dosage form has a multi-layered structure from the upper end to the bottom end: the first layer of the first material, the third layer of the first API, the fifth layer of the second material, the seventh layer of the second API, the sixth layer of the second material, the fourth layer of the first API, and the second layer of the first material;
   wherein the first layer and the second layer are the same, the third layer and the fourth layer are the same, and the fifth layer and the sixth layer are the same; wherein each layer of the seven layers has a thickness of from about 0.05 mm to about 1 mm;
   wherein the cylindrical drug dosage form is produced by three-dimensional (3D) printing, comprising extruding melted first material, melted first API, melted second material, melted second API, melted second material, melted first API, and melted first material sequentially, to form the second layer, the fourth layer, the sixth layer, the seventh layer, the fifth layer, the third layer, and the first layer correspondingly.

2. The cylindrical drug dosage form of claim 1, wherein the first API is the same as the second API.

3. The cylindrical drug dosage form of claim 1, wherein the first API is different from the second API.

4. A cylindrical drug dosage form having an upper end and a bottom end, wherein the cylindrical drug dosage form consists of:
   a cylindrical shell covering the side of the cylindrical drug dosage form but not the upper end and the bottom end, wherein the cylindrical shell consists of an insoluble material selected from the group consisting of poly (ethyl acrylate-methyl methacrylate-trimethyl aminoethyl methacrylate chloride) (poly (EA-MMA-TAMCI)) 1:2:0.2 (molar ratio), poly (EA-MMA-TAMCI) 1:2:0.1 (molar ratio), polyvinyl acetate and povidone mixtures, methacrylic acid ester copolymer, butyl acrylate, methacrylic acid-methylmethacrylate copolymer, ethyl methacrylate-co-methacrylic acid copolymer, butyl acrylate-monobutyl acrylate copolymer, ethyl acrylate-monomethacrylate copolymer, ethyl acrylate-methyl methacrylate copolymer, ethyl acrylate-methyl methacrylate-trimethylaminoethyl methacrylate copolymer, methyl cellulose, ethyl cellulose, hypromellose succinate, hydroxypropyl methylcellulose phthalate, cellulose acetate, polylactic acid, polycaprolactone, carnauba wax, cellulose acetate butyrate, and a combination thereof, wherein the insoluble material does not dissolve in the gastrointestinal tract;
   a first layer and a second layer each consisting of a first material soluble at a first large intestine site, wherein the first material is selected from the group consisting of poly(methacrylic acid-methyl methacrylate) (poly (MA-MMA)) 1:2 (molar ratio), methacrylate copolymer, methacrylic acid-ethyl acrylate copolymer, hydroxypropyl methyl cellulose succinate, and a combination thereof;
   a third, a fourth, and a fifth layer each comprising an API; and
   a sixth and a seventh layer each consisting of a second material soluble at a second large intestine site, wherein the second material is selected from the group consisting of poly (MA-MMA) 1:2 (molar ratio), methacrylate copolymer, methacrylic acid-ethyl acrylate copolymer, hydroxypropyl methyl cellulose succinate, and a combination thereof, wherein the cylindrical drug dosage form has a multi-layered structure from the upper end to the bottom end: the first layer of the first material, the third layer of the API, the sixth layer of the second material, the fourth layer of the API, the seventh layer of the second material, the fifth layer of the API, and the second layer of the first material;

wherein the first layer and the second layer are the same, the third layer and the fifth layer are the same, and the sixth layer and the seventh layer are the same; wherein each layer of the seven layers has a thickness of from about 0.05 mm to about 1 mm;

wherein the cylindrical drug dosage form is produced by 3D printing, comprising extruding melted first material, melted API, melted second material, melted API, melted second material, melted API, and melted first material sequentially, to form the second layer, the fifth layer, the seventh layer, the fourth layer, the sixth layer, the third layer, and the first layer correspondingly.

5. The cylindrical drug dosage form of claim 4, wherein the first material is the same as the second material.

6. A batch of cylindrical drug dosage forms comprising at least 10,000 cylindrical drug dosage forms of claim 1.

7. The batch of cylindrical drug dosage forms of claim 6, wherein at least about 80% of the cylindrical drug dosage forms possess one or more pre-determined characteristics selected from: printing uniformity, precision of layer thickness, precision of layer surface area, precision of layer API mass fraction, precision of cylindrical drug dosage form shape, precision of cylindrical drug dosage form size, precision of cylindrical drug dosage form weight, precision of API amount, and precision of API release profile.

8. A batch of cylindrical drug dosage forms comprising at least 10,000 the cylindrical drug dosage forms of claim 4.

9. The batch of cylindrical drug dosage forms of claim 8, wherein at least about 80% of the cylindrical drug dosage forms possess one or more pre-determined characteristics selected from: printing uniformity, precision of layer thickness, precision of layer surface area, precision of layer API mass fraction, precision of cylindrical drug dosage form shape, precision of cylindrical drug dosage form size, precision of cylindrical drug dosage form weight, precision of API amount, and precision of API release profile.

10. The cylindrical drug dosage form of claim 1, wherein each layer of the seven layers has a thickness of from about 0.1 mm to about 0.6 mm.

11. The cylindrical drug dosage form of claim 4, wherein each layer of the seven layers has a thickness of from about 0.1 mm to about 0.6 mm.

* * * * *